US010072031B1

(12) United States Patent
Merkle et al.

(10) Patent No.: US 10,072,031 B1
(45) Date of Patent: Sep. 11, 2018

(54) SYSTEMS AND METHODS FOR MECHANOSYNTHESIS

(71) Applicants: Ralph C. Merkle, Cupertino, CA (US); Robert A. Freitas, Jr., Pilot Hill, CA (US); Jeremy Barton, Folsom, CA (US); Aru Hill, San Jose, CA (US); Michael Drew, Union City, CA (US); Damian Allis, Syracuse, NY (US); Tait Takatani, Sparks, NV (US)

(72) Inventors: Ralph C. Merkle, Cupertino, CA (US); Robert A. Freitas, Jr., Pilot Hill, CA (US); Jeremy Barton, Folsom, CA (US); Aru Hill, San Jose, CA (US); Michael Drew, Union City, CA (US); Damian Allis, Syracuse, NY (US); Tait Takatani, Sparks, NV (US)

(73) Assignee: CBN Nano Technologies, Inc., Ottawa (CA)

( * ) Notice: Subject to any disclaimer, the term of this patent is extended or adjusted under 35 U.S.C. 154(b) by 0 days.

(21) Appl. No.: 15/153,671

(22) Filed: May 12, 2016

(51) Int. Cl.
*C07F 7/30* (2006.01)
*G01Q 70/08* (2010.01)

(52) U.S. Cl.
CPC .............. *C07F 7/30* (2013.01); *G01Q 70/08* (2013.01)

(58) Field of Classification Search
None
See application file for complete search history.

(56) References Cited

U.S. PATENT DOCUMENTS

| | | | |
|---|---|---|---|
| 4,952,749 | A | 8/1990 | Alexander et al. |
| 4,987,312 | A | 1/1991 | Eigler |
| 5,144,148 | A | 9/1992 | Eigler |
| 5,372,659 | A | 12/1994 | Lamaze et al. |
| 5,824,470 | A | 10/1998 | Baldeschwieler et al. |
| 6,339,227 | B1 | 1/2002 | Ellenbogen |
| 6,348,700 | B1 | 2/2002 | Ellenbogen et al. |
| 6,531,107 | B1 | 3/2003 | Spencer et al. |
| 6,716,409 | B2 | 4/2004 | Hafner et al. |
| 6,835,534 | B2 | 12/2004 | Weiss et al. |
| 7,049,374 | B2 | 5/2006 | Liu et al. |
| 7,309,476 | B2 | 12/2007 | Carlson et al. |
| 7,312,562 | B2 | 12/2007 | Dahl et al. |
| 7,326,293 | B2 | 2/2008 | Randall et al. |
| 7,326,923 | B2 | 2/2008 | Berstis |
| 7,687,146 | B1 | 3/2010 | Freitas |
| 8,171,568 | B2 | 5/2012 | Freitas, Jr. et al. |
| 8,276,211 | B1 | 9/2012 | Freitas, Jr. et al. |
| 9,244,097 | B1 | 1/2016 | Freitas, Jr. et al. |
| 2005/0010213 | A1* | 1/2005 | Stad ............. A61B 17/025 606/53 |
| 2005/0178911 | A1* | 8/2005 | Armand ............. B64C 39/04 244/119 |
| 2009/0056802 | A1 | 3/2009 | Rabani | |
| 2012/0036776 | A1* | 2/2012 | Stevenson ............. B01F 5/0256 48/89 |
| 2015/0308415 | A1* | 10/2015 | Rajasingam ............ B29C 65/78 156/196 |

OTHER PUBLICATIONS

Schleyer et al. Journal of Organic Chemistry, 1966, 31(6), 2014-2015.*
Tostmann, ACS Med. CHem. Lett., 2015, 6, 364-366.*
Freitas et al. Journal of Compoutational and Theoretical Nanoscience (2007), 4(3), 433-442 (derwent abstract).*
Boudjouk et al. Journal of Organometallic Chemistry, 296(3), 1985, 339-349.*
Y. Fukuda, M. Shimomura, G. Kaneda, N. Sanada, V.G. Zavodinsky, I.A. Kuyanov, E.N. Chukurov, "Scanning tunneling microscopy, high-resolution electron energy loss spectroscopy, and theoretical studies of trimethylphosphine (TMP) on a Si(111)-(7x7) surface," Surf. Sci. 442(1999):507-516.
Jinping Peng, Robert A. Freitas Jr., Ralph C. Merkle, James R. Von Ehr, John N. Randall, George D. Skidmore, "Theoretical Analysis of Diamond Mechanosynthesis. Part III. Positional C2 Deposition of Diamond C (110) Surface using Si/Ge/Sn-based Dimer Placement Tools," J. Comput. Theor. Nanosci. 3 (Feb. 2006):28-41.
Berhane Temelso, C. David Sherrill, Ralph C. Merkle, Robert A. Freitas Jr., "High-level Ab Initio Studies of Hydrogen Abstraction from Prototype Hydrocarbon Systems," J. Phys. Chem. A 110 (Sep. 28, 2006):11160-11173.
Berhane Temelso, C. David Sherrill, Ralph C. Merkle, Robert A. Freitas Jr., "Ab Initio Thermochemistry of the Hydrogenation of Hydrocarbon Radicals Using Silicon, Germanium, Tin and Lead Substituted Methane and Isobutane," J. Phys. Chem. A 111(Aug. 15, 2007):8677-8688.
K. Eric Drexler, Nanosystems: Molecular Machinery, Manufacturing, and Computation, John Wiley & Sons, New York, 1992, Chapter 8.
D.M. Eigler, E.K. Schweizer, "Positioning Single Atoms with a Scanning Tunnelling Microscope," Nature 344(Apr. 5, 1990):524-526.
Oyabu, N., Custance, O., et al., (2003), "Mechanical vertical manipulation of selected single atoms by soft nanoindentation using near contact atomic force microscopy," Phys. Rev. Lett. 90(May 2, 2003):176102.
Merkle, Ralph C. (1997) "A proposed 'metabolism' for a hydrocarbon assembler," Nanotechnology 8 (1997):149-162.
M.C. Hersam, G.C. Abeln, J.W. Lyding, "An approach for efficiently locating and electrically contacting nanostructures fabricated via UHV-STM lithography on Si(100)," Microelectronic Engineering 47(Jun. 1999):235-237.
D.H. Huang, Y. Yamamoto, (1997) "Physical mechanism of hydrogen deposition from a scanning tunneling microscopy tip," Appl. Phys. A 64(Apr. 1997):R419-R422.

(Continued)

*Primary Examiner* — Clinton A Brooks

(57) ABSTRACT

Systems and methods for mechanosynthesis including those that avoid the need for a bootstrap process, avoid the need to build tips via mechanosynthesis, avoid the need for charging tips with feedstock during a build sequence, avoid the need to dispose of reaction byproducts, reduce the design complexity of new tips, and reduce or avoid the need for multiple positional means or tip switching.

6 Claims, 31 Drawing Sheets

(56) References Cited

OTHER PUBLICATIONS

J. Murota, M. Sakuraba, (2004) "Atomically controlled processing for high-performance Si-based devices," Tohoku-Cambridge Forum (Hall in Peterhouse, University of Cambridge, Organizers: M. Koyanagi, W. I. Milne), International Workshop on Nano-Technology, Nano-Materials, Nano-Devices, and Nano-Systems, Jun. 11, 2004.
Celotta, R. J., Balakirsky, S. B., et al. (2014), "Invited Article: Autonomous assembly of atomically perfect nanostructures using a scanning tunneling microscope", Rev Sci Instrum.
Ceria, P., Ducourtieux, S., et al. (2015), "Estimation of the measurement uncertainty of LNE's metrological Atomic Force Microscope using virtual instrument modeling and Monte Carlo Method".
Dai, G., Zhu, F., et al. (2015), "High-speed metrological large range AFM", Measurement Science and Technology 26. IOP Publishing. UK.
Y. Fukuda, M. Shimomura, G. Kaneda, N. Sanada, V.G. Zavodinsky, I.A. Kuyanov, E.N. Chukurov, "Scanning tunneling microscopy, high-resolution electron energy loss spectroscopy, and theoretical studies of trimethylphosphine (TMP) on a Si(111)-(7×7) surface," Surf. Sci. 442(1999):507-516.
M.J. Bronikowski, R.J. Hamers, "The chemistry of gallium deposition on Si(001) from trimethylgallium: an atomically resolved STM study," Surf. Sci. 348(Mar. 10, 1996):311-324.
D.M. Gruen, S.Liu, A. R. Krauss, X.Pan, "Buckyball microwave plasmas: Fragmentation and diamond-film growth," J. Appl. Phys. 75(1994):1758-1763.
Eder, F. R., Kotakoski, J., et al. (2013), "Probing from both sides: reshaping the graphene landscape via face-to-face dual-probe microscopy", Nano Letters.
Guangquan Lu, John E. Crowell, "The adsorption and thermal decomposition of digermane on Ge(111)," J. Chem. Phys. 98(Feb. 15, 1993):3415-3421.
N. Oyabu, O. Custance, M. Abe, S. Moritabe, "Mechanical Vertical Manipulation of Single Atoms on the Ge (111)-c(2×8) Surface by Noncontact Atomic Force Microscopy," Abstracts of Seventh International Conference on Non-Contact Atomic Force Microscopy, Seattle, Washington, USA, Sep. 12-15, 2004.
P.D. Nellist, M.F. Chisholm, N. Dellby, O.L. Krivanek, M.F. Murfitt, Z.S. Szilagyi, A.R. Lupini, A. Boresivich, W.H. Sides, Jr., S.J. Pennycock, "Direct Sub-Angstrom Imaging of a Crystal Lattice," Science 305 (Sep. 17, 2004):1741.
G. Basile, P. Becker, A. Bergamin, G. Cavagnero, A. Franks, K. Jackson, U. Kuetgens, G. Mana, E.W. Palmer, C.J. Robbie, M. Stedman, J. Stumpel, A. Yacoot, G. Zosi, "Combined optical and X-ray interferometry for high-precision dimensional metrology", Proc. R. Soc. Lond. A (2000) 456, 701-729.
Y. Sugimoto, P. Pou, O. Custance, P. Jelinek, M. Abe, R. Perez, S. Morita, "Complex Patterning by Vertical Interchange Atom Manipulation Using Atomic Force Microscopy", Science 322, 413 (2008).
Artyukhov, V. I., "A six degree of freedom nanomanipulator design based on carbon nanotube bundles." Nanotechnology 21(38): 9 (2010).
Duwez, A., Cuenot, S., et al., "Mechanochemistry: targeted delivery of single molecules." Nature Nanotechnology 1(2): 122-125 (2010).
Ho, W. and Lee, H., "Single bond formation and characterization with a scanning tunneling microscope." Science (286): 1719-1722 (2010).
Tarasov, D., Akberova, N., et al. (2010). "Optimal Tooltip Trajectories in a Hydrogen Abstraction Tool Recharge Reaction Sequence for Positionally Controlled Diamond Mechanosynthesis." J. Comput. Theor. Nanosci. 7(2): 325-353.
Yang, S. H., Kim, Y.-S., et al. (2012). "Microelectromechanical systems based Stewart platform with sub-nano resolution." Appl. Phys. Lett. 101(6): 5.
Johannes, M. S. (2006). "Automated CAD/CAM-based nanolithography using a custom atomic force microscope." IEEE Transactions on Automation Science and Engineering 3(3): 236-239.
Ramachandrann, T., Baur, C., et al. (1998). "Direct and Controlled Manipulation of Nanometer-Sized Particles Using the Non-Contact Atomic Force Microscope." Nanotechnology(9): 237-245.
Tay, A. B. H. and Thong, J. T. L. (2004). "Fabrication of super-sharp nanowire atomic force microscope using a field emission induced growth technique." Review of Scientific Instruments 75(10).
Wong, S., Woolley, A., et al. (1999). "Functionalization of carbon nanotube AFM probes using tip-activated gases." Chemical Physics Letters(306): 219-225.
Hafner, J., Cheung, C., et al. (2001). "Structural and Functional Imaging with Carbon Nanotube AFM Probes." Progress in Biophysics & Molecular Biology 1(77): 73-110.
Chen, H. (2006). "CAD-guided automated nanoassembly using atomic force microscopy-based nonrobotics." IEEE Transactions on Automation Science and Engineering 3(3): 208-217.
Grandbois, M., Dettmann, W., et al. (2000). "Affinity Imaging of Red Blood Cells Using an Atomic Force Microscope." Journal of Histochemistry & Cytochemistry(48): 719-724.
Morita, S., Sugimoto, Y., et al. (2004). "Atom-selective imaging and mechanical atom manipulation using the non-contact atomic force microscope." J. Electron Microsc. 53(2): 163-168.
Lapshin, R. V. (2004), "Feature-oriented scanning methodology for probe microscopy and nanotechnology", Nanotechnology.
Lapshin, R. V. (2007), "Automatic drift elimination in probe microscope images based on techniques of counter-scanning and topography feature recognition", Measurement Science and Technology.
Lapshin, R. V. (2011), "Feature-Oriented Scanning Probe Microscopy", Encyclopedia of Nanoscience and Nanotechnology.
Lawall, J. R. (2005), "Fabry-Perot metrology for displacements up to 50 mm", J. Opt. Soc. Am. A.
Morita, S., Sugimoto, Y., et al. (2004), "Atom-selective imaging and mechanical atom manipulation using the non-contact atomic force microscope", J. Electron Microsc.
Sidler, K., Cvetkovic, N. V., et al. (2010), "Organic thin film transistors on flexible polyimide substrates fabricated by full-wafer stencil lithography", Sensors and Actuators A: Physical 162. Elsevier.
Sugimoto, Y., Jelinek, P., et al. (2007), "Mechanism for Room-Temperature Single-Atom Lateral Manipulations on Semiconductors using Dynamic Force Microscopy", Physical Review Letters.
Sugimoto, Y., Pou, P., et al. (2008), "Complex Patterning by Vertical Interchange Atom Manipulation Using Atomic Force Microscopy", Science.
Vazquez-Mena, O., Gross, L., et al. (2015), "Resistless nanofabrication by stencil lithography: A review", Microelectronic Engineering 132. Elsevier.
Yesilkoy, F., Flauraud, V., et al. (2016), "3D nanostructures fabricated by advanced stencil lithography", Nanoscale 8. Royal Society of Chemistry. UK.
Zahl, P., Bammerlin, M., et al. (2005), "All-in-one static and dynamic nanostencil atomic force microscopy/scanning tunneling microscopy system", Review of Scientific Instruments 76. AIP Publishing. U.S.
Pierce, C.J. and M.K. Hilinski, Chemoselective hydroxylation of aliphatic sp3 C-H bonds using a ketone catalyst and aqueous H2O2. Org Lett, 2014. 16(24): p. 6504-7.
Grillaud, M. and A. Bianco, Multifunctional adamantane derivatives as new scaffolds for the multipresentation of bioactive peptides. Journal of Peptide Science, 2014.
Maison, W., et al., Synthesis of Functionalized Adamantane Derivatives: (3 +1)-Scaffolds for Applications in Medicinal and Material Chemistry. Synthesis, 2013. 45(11): p. 1452-1461.
Shokova, E.A. and V.V. Kovalev, Adamantane functionalization. Synthesis of polyfunctional derivatives with various substituents in bridgehead positions. Russian Journal of Organic Chemistry, 2012. 48(8): p. 1007-1040.
Senchyk, G., et al., 1,2,4-Triazole functionalized adamantanes: A new library of polydentate tectons for the designing structures of coordination polymers. Dalton Transactions, 2012. p. 1-19.
Chalifoux, W.A., et al., Adamantyl-endcapped polyynes. Journal of Physical Organic Chemistry, 2012.25(1): p. 69-76.

(56) References Cited

OTHER PUBLICATIONS

Lamanna, G., et al., HYDRAmers: design, synthesis and characterization of different generation novel Hydra-like dendrons based on multifunctionalized adamantane. Chem Commun (Camb), 2011. 47(31): p. 8955-7.

Pannier, N. and W. Maison, Rigid C3-Symmetric Scaffolds Based on Adamantane. European Journal of Organic Cemistry, 2008. 2008(7): p. 1278-85.

Nasr, K., et al., Rigid Multivalent Scaffolds Based on Adamantane. J. Org. Chem., 2008. 73: p. 1056-62.

Maison, W., J. Frangioni, and N. Pannier, Synthesis of Rigid Multivalent Scaffolds Based on Adamantane. Organic Letters, 2004. 6(24): p. 4567-69.

Izumi, H. and S. Futamura, Convenient synthesis of 3,5,7-trimethyl-1-azonia-adamantanes. ARKIVOC, 2000: p. 6-13.

Shvekhgeimer, M., Adamantane derivatives containing heterocyclic substituents in the bridgehead positions. Synthesis and properties. Russian Chemical Reviews, 1996. 65(7): p. 554-598.

Sasaki, T., Heteroadamantane. Advances in Heterocyclic Chemistry, 1982. 30: p. 79-126.

Bagrii, E.I., A.I. Nekhaev, and A.L. Maksimov, Oxidative functionalization of adamantanes (review). Petroleum Chemistry, 2017. 57(3): p. 183-197.

Averina, N.V. and N.S. Zefirov, Advances in the Synthesis of Heteroadamantanes. Uspekhi Khimii, 1976. 45: p. 544-556.

\* cited by examiner

M = Si, Ge
R = -H, -CH$_3$

SYSTEMS AND METHODS FOR MECHANOSYNTHESIS

CROSS-REFERENCE TO RELATED APPLICATIONS

Not applicable.

FEDERALLY SPONSORED RESEARCH

Not applicable.

SEQUENCE LISTING OR PROGRAM

Not applicable.

FIELD OF INVENTION

The present invention is directed to systems and methods that perform mechanosynthesis, including the use of modular tips and tips bound to a surface.

BACKGROUND OF THE INVENTION

Scanning Probe Microscopes (SPM, including e.g., AFM, SFM, and STM) have long been used, in conjunction with ultra-sharp tips, to move individual atoms or molecules to precise locations. When such site-specific positioning (and force, if necessary) is used to make or break chemical bonds, this is referred to as mechanosynthesis. (Oyabu, Custance et al., "Mechanical vertical manipulation of selected single atoms by soft nanoindentation using near contact atomic force microscopy," Phys. Rev. Lett., 17, 2003; Morita, Sugimoto et al., "Atom-selective imaging and mechanical atom manipulation using the non-contact atomic force microscope," J. Electron Microsc., 2, 2004; Oyabu, Custance et al., "Mechanical Vertical Manipulation of Single Atoms on the Ge(111)-c(2×8) Surface by Noncontact Atomic Force Microscopy," Seventh International Conference on non-contact Atomic Force Microscopy, Seattle, Wash., 2004; Sugimoto, Jelinek et al., "Mechanism for Room-Temperature Single-Atom Lateral Manipulations on Semiconductors using Dynamic Force Microscopy," Physical Review Letters, 10, 2007; Sugimoto, Pou et al., "Complex Patterning by Vertical Interchange Atom Manipulation Using Atomic Force Microscopy," Science, 2008).

Conceptually, mechanosynthesis might be broken into several components: A source of atoms or molecules ("feedstock") used to build (including modifying) workpieces; a place where feedstock is stored while awaiting use (a "feedstock depot"); the product being built (a "workpiece"); a place to store reaction byproducts (a "trash depot"); a structure that directly performs mechanosynthesis reactions (a "tip"); a surface (or "presentation surface"), which can serve several purposes including serving as a feedstock depot and a surface upon which to build the workpiece; and a positional means (e.g., an SPM probe) which controls the relative position of, e.g., tips and workpieces, to facilitate the desired reactions.

Not all systems will have each of these parts as discrete entities, and some will be missing completely. For example, in some mechanosynthesis experiments, one atom was interchanged for another on a surface. In such cases, the presentation surface, feedstock depot, and workpiece were one and the same. In this work, there was no trash depot, since there were no reaction byproducts. Also, note that in some previous examples of such work, only one tip was required because only one or two distinct reactions were being performed (although they may have occurred many times each), and one tip sufficed for all reactions.

However, as the desired reactions become more varied, greater flexibility can be obtained by having a distinct feedstock, feedstock depot, trash depot, presentation surface, and workpiece. Also, multiple tips may be required, each designed to facilitate a particular reaction or set of reactions. Note that a requirement for multiple tips implies some way to bring multiple tips to bear for sequential or parallel operation (e.g., multiple positional means, or some way to swap tips on a single positional means).

As an example of systems that use discrete feedstock, feedstock depots, presentation surfaces, workpieces, and multiple tips, among other possible components, methods for the creation of atomically-precise tips from non-atomically-precise tips ("bootstrapping") have been described, along with numerous mechanosynthetic reactions which employ a variety of tips, and methods for using multiple reactions to form build sequences for creating complex workpieces (e.g., see patent documents U.S. Pat. No. 9,244,097, US Patent Publication No. 20150355228, US Patent Publication No. 20130184461, US Patent Publication No. 20130178627, US Patent Publication No. 20130178626, U.S. Pat. No. 8,276,211, and U.S. Pat. No. 8,171,568).

Systems capable of more varied build sequences tend to have higher chemical and equipment complexity. For example, chemically, bootstrapping is not a simple process. Neither is the design of new tips, along with the reactions to regenerate tips which are to be used multiple times. Further, feedstock needs to be provided in a chemically-appropriate manner (e.g., feedstock needs to be provided in a manner that will not allow it to react inappropriately with itself, other feedstock, the feedstock depot, or in ways counter to its designated tip binding modes).

In terms of equipment, a larger number of reactions, more types of feedstock, and larger workpieces can all require a larger presentation surface. A larger presentation surface means that the positional means must maintain sub-Angstrom accuracy over longer distances. Additionally, if multiple tips are required, some solution to the problem of using each tip as needed must be provided.

The chemical problems can and have been addressed, as shown by the cited references. And, the equipment problems can all be addressed.

For example, while obtaining the requisite accuracy can be challenging, it is by no means infeasible. Software can be used to enhance the positional accuracy of mechanosynthesis equipment either by correcting for various types of positional errors (Ceria, Ducourtieux et al., "Estimation of the measurement uncertainty of LNE's metrological Atomic Force Microscope using virtual instrument modeling and Monte Carlo Method," 2015) or through the use of image recognition, allowing the location of a tip to be determined based on the observed surface features. (Lapshin, "Feature-oriented scanning methodology for probe microscopy and nanotechnology," Nanotechnology, 9, 2004; "Automatic drift elimination in probe microscope images based on techniques of counter-scanning and topography feature recognition," Measurement Science and Technology, 3, 2007; "Feature-Oriented Scanning Probe Microscopy," Encyclopedia of Nanoscience and Nanotechnology, 2011; Celotta, Balakirsky et al., "Invited Article: Autonomous assembly of atomically perfect nanostructures using a scanning tunneling microscope," Rev Sci Instrum, 12, 2014)

Hardware can also be used to refine microscope tip position. Many microscope systems are open-loop, meaning they do not employ metrology to correct tip position. However, closed-loop systems which do employ metrology are available. For example, AttoCube's (attocube systems AG, Muenchen, Germany) attoDRY LAB claims <1 nm sensor resolution with no piezo hysteresis, attained using interferometry. And, multi-tip systems are also available. And, in addition to literature describing the custom fabrication of multi-probe SPMs (Eder, Kotakoski et al., "Probing from both sides: reshaping the graphene landscape via face-to-face dual-probe microscopy," Nano Letters, 5, 2013), various vendors sell systems that have either more than one probe, or the ability to swap tips on a single probe. For example, the MultiView 4000 (NANONICS IMAGING LTD. HEADQUARTERS, Israel), which can employ up to 4 probes, the "Titanium" (NT-MDT Co., Building 100, Zelenograd, Moscow 124482, Russia), which has a cartridge that can automatically swap between 38 probes, and the LT QuadraProbe™ (RHK Technology, Inc, Troy, Mich. 48083 USA) which includes 4 probes.

However, even though the chemical and equipment challenges inherent in complex mechanosynthesis can be solved, the solutions can increase the cost and complexity of the systems, slow their functioning, and increase the difficulty of designing and manufacturing new tips, reactions, and build sequences. Other solutions, including simply avoiding some of the problems in the first place, would therefore be useful.

BRIEF SUMMARY OF THE INVENTION

The present invention is directed to systems, methods, and products for the fabrication of atomically-precise tips used for mechanosynthesis, provisioning such tips in a manner which increases the efficiency of mechanosynthesis, and provides a novel design paradigm for the creation of new tips. Aspects of the invention also allow for reduced hardware and software complexity, and positional means optimized for mechanosynthesis.

BRIEF DESCRIPTION OF DRAWINGS

For a more complete understanding of the present invention, reference is now made to the following descriptions taken in conjunction with the accompanying drawings, in which.

DETAILED DESCRIPTION OF THE INVENTION

Definitions

Figure 1:
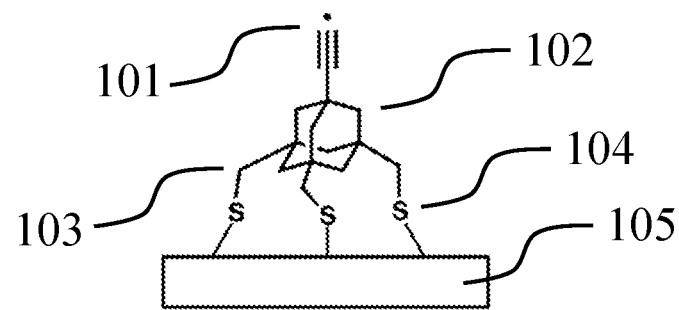
FIG. 1 depicts the modular parts of an exemplary tip.

The following definitions are used herein:

An "adamantane" molecule comprises a 3D cage structure of ten carbon atoms, each terminated with one or two hydrogen atoms, having the chemical formula C10H16 and representing the smallest possible unit cage of crystalline diamond.

An "adamantane-like" structures include one or more adamantanes, one or more adamantanes where one or more atoms have been substituted with atoms or molecular fragments of like or similar valence, including e.g., Nitrogen, Oxygen, and Sulfur-substituted variations, and similar molecules comprising polycyclic or cage-like structures. By way of example, and not of limitation, adamantane-like structures would include adamantane, heteroadamantanes, polymantanes, lonsdaleite, crystalline silicon or germanium, and versions of each of the foregoing where, for example, Fluorine is used for termination instead of Hydrogen, or where termination is incomplete.

An "atom" includes the standard use of the term, including a radical, which, for example, may be just a proton in the case of $H^+$.

"Atomically-precise" means where the position and identity of each atom is known to a precision adequate to enable a site-specific mechanosynthetic reaction.

The "bridgehead" position in an adamantane-like molecular structure refers to a structural atom that is bonded to three other structural atoms and may be terminated by one or more nonstructural atoms. This is contrasted with a "sidewall" position which refers to a structural atom that is bonded to two other structural atoms and is terminated by one or more nonstructural atoms.

A "build sequence" is one or more mechanosynthetic reactions arranged in an ordered sequence that permits the assembly, disassembly, or modification of a workpiece.

A "chemical bond" is an interatomic covalent bond, an interatomic ionic bond, or interatomic coordination bond, as these terms are commonly understood by practitioners skilled in the art.

A "chemical reaction" is said to occur when chemical bonds are formed, broken, or altered.

"Diamond" is a crystal of repeating adamantane cage units arranged in various well-known crystallographic lattice geometries.

"Diamondoid" materials include any stiff covalent solid that is similar to diamond in strength, chemical inertness, or other important material properties, and possesses a three-dimensional network of bonds. Examples of such materials include but are not limited to (1) diamond, including cubic and hexagonal lattices and all primary and vicinal crystallographic surfaces thereof, (2) carbon nanotubes, fullerenes, and other graphene structures, (3) several strong covalent ceramics of which silicon carbide, silicon nitride, and boron nitride are representative, (4) a few very stiff ionic ceramics of which sapphire (monocrystalline aluminum oxide) is representative, and (5) partially substituted variants of the above that are well-known to those skilled in the art.

"Feedstock" is the supply of atoms used to perform mechanosynthetic reactions on a workpiece. Feedstock may take the form of an atom or atoms (a group or molecule), including radicals (e.g., .GeH2, .CH2).

A "handle structure" comprises a plurality of atoms whose bonding pattern is not altered during a site-specific mechanosynthetic chemical reaction and whose primary function is to hold a tip(s) or workpiece(s) to facilitate a mechanosynthetic chemical reaction to when the handle structure is manipulated by a positional device. Handle structure may include the null case.

An "inert environment" includes, but is not limited to, UHV, helium, neon, or other noble gases either individually or in combination, or other gases or liquids that do not react with the tip, feedstock, or workpiece during mechanosynthetic operations.

"Inverted mode" is the strategy of performing mechanosynthesis by moving the workpiece to the appropriate tip, rather than the "conventional mode" of moving a tip to a stationary workpiece.

"Mechanical force" may include applied mechanical forces having positive, negative, or zero magnitude. Chemical reactions driven by the application of mechanical force include reactions that are (1) driven through its reaction barrier by mechanically forcing reactants or products through the transition state, or (2) driven away from an undesired reaction by mechanically restraining potentially reactive sites from attaining closer physical proximity, or (3) allowed to occur by bringing potentially reactive sites into closer physical proximity when zero mechanical force is required to do so, as for example when no reaction barrier exists.

"Mechanosynthesis" is the use of positional control and mechanical force to facilitate one or more site-specific chemical reactions involved in the creation of a workpiece. The use of voltage biases combined with mechanical force-based mechanosynthesis is not required, but is included in the definition of mechanosynthesis.

A "mechanosynthetic reaction" (sometimes referred to as a "reaction" when context makes it clear that the reaction is mechanosynthetic) is a chemical reaction carried out using mechanosynthesis.

A "meta-tip" is a tool to which multiple tips are attached. For example, a meta-tip could be prepared using a conventional SPM probe with a flat surface on the end, which is then functionalized with the desired tips.

A "modular tip" is a synthetic tip with a modular design, where modules include an active site, a body, and legs (which may have linkers). Tips for donation reactions may also have a feedstock module. A modular tip may be referred to as simply a "tip" when context makes the type of tip clear.

A "positional device" is a device capable of exerting atomically-precise positional control on a mechanosynthetic tip, tool, or workpiece, and may include, but is not limited to, scanning probe microscopes (SPM) and atomic force microscopes (AFM) and related devices, a miniaturized or MEMS-scale SPM or AFM, a robotic arm mechanism of any size scale, or other appropriate manipulation system capable of atomically-precise positional control and appropriate force application.

A "presentation surface" is a surface which can be used for, among other purposes, binding tips for use in mechanosynthesis, and as a base on which to build a workpiece. Although generally monolithic, there is no reason a presentation surface cannot be composed of more than one material (e.g., gold and silicon could both be used where each has advantageous aspects), or composed of multiple non-adjacent surfaces. May be referred to simply as a "surface" when context makes the meaning clear. Presentation surfaces include the appropriate areas on meta-tips.

"Site-specific" refers to knowing, and being able to constrain, with a desired degree of reliability, the position at which a mechanosynthetic reaction takes place.

A "structural atom" in an adamantane-like molecular structure refers to an atom comprising the cage framework, for example a carbon atom in an adamantane molecule. More generally, a structural atom is an atom that comprises part of the backbone or overall structure in a highly-bonded molecule.

A "synthetic tip" is an atomically-precise tip manufactured via a bulk method, such as gas or solution-phase chemistry, rather than via mechanosynthesis. May be referred to as simply a "tip" when context makes the type of tip clear.

A "terminating atom" refers to an atom that does not serve as a structural atom but absorbs unused valences of a structural atom. For example, a hydrogen atom in an adamantane molecule.

A "three-dimensional" workpiece means a workpiece including a lattice of atoms whose covalent structure occupies three dimensions, considering atoms as points, and discounting torsion angles. Under this definition, for example, proteins would be two dimensional, as would a plane of graphene. A covalent network solid or a carbon nanotube would be three-dimensional.

A "tip" is a device for facilitating mechanosynthetic reactions which includes one or more "active" atoms or sites whose bonding pattern or electronic state is altered during a mechanosynthetic operation, and one or more "support" atoms whose bonding pattern or electronic state is not altered during a mechanosynthetic operation. The support atoms function to hold the active atoms in position.

"Tip swapping" is the process of connecting a new tip to a positional means during a build sequence where said positional means already had a previous tip to which it was connected.

A "tool" comprises a tip, potentially bonded to a handle, controlled by a positional device or means.

A "workpiece" is an apparatus, article of manufacture, or composition of matter, built via mechanosynthesis. A system may have more than one workpiece. A workpiece may be connected to, but does not include, other structures that were not created via mechanosynthesis, such as a support substrates, feedstock depots, or tethered pre-existing structures.

Chemical Structure and Scientific Notation

A dot (".") is may be used in chemical structures herein to represent an electron, as in the radical group ".CH2". For ease of typesetting, the notation herein generally omits subscript or non-standard characters. Superscript may be written using the "^" character when required for clarity.

Synthetic Tips

The instant invention addresses many problems related to mechanosynthesis, with at least some embodiments having one or more of the following benefits: avoiding the need for a bootstrap process, avoiding the need to build tips via mechanosynthesis, avoiding the need for charging tips with feedstock during a build sequence, avoiding the need to dispose of reaction byproducts, reducing the design complexity of new tips, and reducing or avoiding the need for multiple positional means or tip switching. In addition, embodiments of the invention allow for faster reaction throughput and longer tip travel distances while still maintaining sub-Angstrom accuracy.

Previous literature described (see, e.g., U.S. Pat. No. 9,244,097) a bootstrap process to facilitate the creation of atomically-precise tips from atomically-imprecise tips using mechanosynthesis. As an alternate method of directly preparing atomically-precise tips, we describe the bulk synthetic chemical preparation (and if appropriate, activation or depassivation) of various atomically-precise tips, which can then be bonded to a presentation surface or tool. In this way, atomically-precise tips can be obtained without first using atomically-imprecise tips.

Not only can synthetic tips be prepared in a different manner than previously-known tips, but the manner in which synthetic tips are used can vary from the way previously-known tips are used in the literature. While synthetic tips could be used in the same manner as previously-described tips (e.g., via affixing a single synthetic tip to a handle), bulk preparation also allows other strategies to be employed.

For example, previous proposals describe rechargeable tips, using strategies that use a relatively small number of tips over and over again during a build sequence. Because synthetic tips are available in very large numbers after synthesis, a large number of synthetic tips could be affixed to a presentation surface. The synthetic tips can be pre-charged (meaning, the tips are already in the chemical state desired to carry out the intended reactions, such as already being bonded to feedstock), and they can include large numbers of every type of tip required for a given build sequence. In this way, the presentation surface can serve purposes including being a feedstock depot (the synthetic tips already being charged with their feedstock), a trash depot (e.g., radical tips could be used to bind undesired atoms), and a varied collection of tips that can carry out all necessary reactions. Using a large number of synthetic tips allows each tip to be disposable, rather than requiring recharge for subsequent use, avoiding the need to design and perform recharge operations. Note that in this scenario the workpiece could be moved to the desired tip ("inverted mode"), rather than vice versa ("conventional mode"). Inverted mode is not necessary, but may be easier to implement on some equipment.

Conceptually, if the workpiece moves and the presentation surface is stationary, one could think of a build sequence as a workpiece moving around a presentation surface, aligning itself with a desired tip, and then being brought into contact with that tip with sufficient force to trigger the desired reaction. The tip that was used is then spent, but the presentation surface can easily provide large numbers of tips (e.g., depending on the size of the surface and the tip density, greater than a thousand, or even a million, or a billion tips could be available). The build sequence proceeds by then aligning the workpiece with the next appropriate tip and bringing them together. This process repeats until the entre workpiece is built.

Other variations on this concept are also possible, including a tool which holds multiple tips (a "meta-tip"). Such designs may be more efficient than a tool holding a single tip because multiple reactions could be performed without requiring tips swapping or tip recharge. Whether the tips reside on a presentation surface, or on a tool, and whether the presentation surface, the tool, the workpiece, or some combination thereof are coupled to positional means, the overarching point is a design which has at least some of the following characteristics and advantages, among others.

First, a large number (e.g., more than a thousand even on a relatively small surface, while over a million or even over a billion is feasible on a larger presentation surface) of tips may be available, whether on, for example, a conventional presentation surface (e.g., a silicon wafer) or a "meta-tip." These tips may all be the same, or could be of different types. If multiple tip types are present, they could be randomly intermingled, segregated by sector or position, or the tips could be laid out in an order which maximizes the efficiency of a build sequence (for example, by arranging different tip sectors in a manner that minimizes the movement required to perform the mechanosynthetic operations to build a particular workpiece, or considering a more general design, locating tips that are apt to be used more frequently closer to the workpiece, or locating tip sectors concentrically around a workpiece to minimize total tip to workpiece distance regardless of the order of reactions).

Second, due to the large number of tips that are accessible to the system, tip recharge may be reduced or eliminated during a build sequence. Each tip can be used once, and then ignored once it is spent. By eliminating recharge reactions, shorter, faster build sequences are facilitated. If additional tips were still required, e.g., for a workpiece requiring a number of tips beyond that which are available, the strategy of mounting a large number of tips, preferably in their ready-to-use state, on a surface, allows the bulk replacement of tips by swapping in a new surface. In this scenario, tip recharge is not completely eliminated, but it is greatly reduced.

Third, tips do not have to be swapped for chemical diversity because every type of tip needed for a given build sequence can be present somewhere on the presentation surface. This reduces or eliminates the need for multiple positional means, or the need to change the tool connected to a single positional means.

Fourth, large numbers of atomically-precise tips can be prepared and affixed via bulk chemical reactions (and similarly bulk activated, if required). This eliminates the need for a bootstrap process that uses non-atomically-precise tips to create atomically-precise tips. Exemplary synthetic pathways for multiple synthetic tips are described herein.

Fifth, system complexity is kept relatively low, and the number of tips and feedstock moieties available can be relatively high, as compared to other proposals for providing feedstock via, for example, methods which require cartridges or conveyor belts (Rabani, "Practical method and means for mechanosynthesis and assembly of precise nanostructures and materials including diamond, programmable systems for performing same; devices and systems produced thereby, and applications thereof," US Patent App 20090056802, United States, 2009).

Surface-Mounted Tips

Synthetic tips, if properly designed, can be chemically bound to a presentation surface, or "surface-mounted." In addition to being amenable to synthesis using traditional chemistry, and carrying out one or more mechanosynthetic reactions, surface-mounted tips are designed to allow efficient bonding to a presentation surface or handle structure (often in large quantity).

Surface-mounted tips differ from conventional tips in that they are not simply integral to a handle structure (e.g., commercially available tips often have a tip where the crystal structure of the tip is contiguous with the handle structure; essentially the tip is just the end of the handle structure), nor are they a handle structure to which only a trivial functionalization has been added (e.g., bonding a single CO to the end of an existing tip is a common technique to increase resolution). Surface-mounted tips differ from previously-proposed mechanosynthetically-created tips in that they do not require mechanosynthesis to manufacture (which has not only process implications, but structural and chemical implications since this requires that surface-mounted tips be able to bind to the desired surface without the aid of mechanosynthesis). Given this, while surface-mounted tips may look similar to other tips described in the literature, the requirements for the design of tips which are to be surface-mounted are substantially different.

Binding orientation is one issue that must be addressed when designing surface-mounted tips. It would be preferable that the tips only be able to affix themselves to a surface in a manner that renders them properly oriented for use in mechanosynthetic reactions (although multiple possible orientations could be acceptable given the number of redundant tips that could be present—the system could then scan to identify and use only tips in the desired orientation, but this reduces efficiency).

Active sites and legs are discussed in more detail herein, but are major factors in ensuring that correct binding orientation is obtained. For example, tips with radical active sites will be highly reactive in their active form. Due to this high reactivity, the active site may bind to the presentation surface instead of the legs. If this happens, the tip would end up bound to the presentation surface upside down. Reactive sites may also form bonds to other parts of the same tip, or may form bonds to other tips, such as two tips dimerizing. This problem may be avoided in the case of reactive active sites by binding the tip to the presentation surface with the active sites neutralized. The active sites can then be activated after leg binding. A similar issue presents itself with respect to the legs. The legs (or leg linkers) need to be reactive enough that they will bind to the presentation surface, but they must resist pathological reactions with themselves or other tips (e.g., forming a leg-leg bond instead of a leg-surface bond, or undergoing any other undesired reactions).

Of course, there are other design consideration for tips, including that they perform the desired reactions reliably during a build sequence, but the above concerns are unique to bulk-synthesized, surface-mounted tips. Tips created using mechanosynthesis can largely avoid these problems via positional specificity. Further, mechanosynthetically-created tips have different design constraints due to the different methods of construction (e.g., as will be explained later, one way to attach synthetic tips to a surface involves chlorinating the surface, which introduces its own design constraints; chlorination could be avoided or removed as needed using mechanosynthesis). Although for different reasons, conventional tips avoid such problems (and therefore design constraints) as well. For example, tips which are simply ultra-sharp continuations of a handle structure need not worry about orientation or other pathological binding considerations.

Modular Tip Design

As will be seen in subsequent examples, surface-mounted tips can be thought of as being modular. Each tip can be thought of as having an active site (one or more atoms that bind a desired atom or group of atoms, which could be, e.g., feedstock for a donation reaction, or some moiety to be removed from a workpiece for an abstraction reaction), a body (adamantane or an adamantane derivative in our examples, but other structures obviously could be used), and one or more legs that serve to attach the tip to a surface. The feedstock of a tip could also be considered a module, as could the surface, which, although not technically part of the tip, can be important to tip design and function.

To aid in understanding how tips function, and how they can be rationally designed, considerations pertinent to each module are described below. Note that the specific examples presented use adamantane, or adamantane-like bodies. Many reactions for functionalizing adamantanes are known, and their stiffness, small size, computational tractability and other favorable characteristics lead us to use these structures as exemplary tips, although obviously many different molecules, including other adamantane-like structures, could serve the same purpose.

The active site's main characteristic is that it reliably facilitate the desired reaction on a workpiece. However, how to efficiently synthesize and deliver tips to a surface, and prepare them for use, must be considered in their design. Particularly when containing a radical in its ready-to-use state, a tip may incorporate a protective cap (what in solution-phase chemistry is commonly referred to as a "protecting group"). This cap reduces the active site's reactivity prior to use to avoid, for example, tip-tip dimerization, binding of the active site to the surface, or other undesired reactions. However, the cap must be removable so that the tip can be activated for use. One way to do this is to make the cap photo-cleavable, but obviously other methods are possible as long as they selectively remove the desired caps without harming any tips that may be present.

The body serves as a point of attachment for the active site and legs, and can also serve to tune the active site, and to isolate it from other chemical influences. With respect to tuning the active site, for example, substitutions which alter bond lengths, angles, or electronegativity may be used to increase or decrease the affinity of the active site for its feedstock or whatever moiety it is intended to bind. With respect to isolation, the body provides chemical isolation from, for example, the legs. Such isolation is one of the aspects of this modular design paradigm that eases the design of new tips by allowing modules to be put together combinatorially. For example, if an active site and body combination that accomplish the desired reaction are already known, but one desires to use a different surface which necessitates different legs or linkers, it is likely that the new parts can be swapped in without redesign of the body and active site. If the legs were connected directly to the active site, their chemical nature would tend to have more of an effect on the active site, potentially requiring more redesign. Another characteristic of the body is that it is preferably rigid. A rigid body, while not required, will tend to be more versatile because a rigid body will better resist deformation when pressed on during reaction with a barrier that must be overcome.

The legs serve to attach the body to the surface. The legs preferably have a geometry that permits them to bind the body to a surface without excessive strain, including surfaces that are functionalized prior to leg attachment. Functionalized surfaces, such as chlorinated Si, may make longer legs preferable because the, e.g., Cl atoms, can be directly under the tip body, make some clearance between the body of the tip and Si itself preferable. Legs are also preferably fairly rigid, and strong enough so that reactions require the application of force to overcome a barrier proceed reliably rather than the tip tilting, otherwise moving, or breaking a leg bond. While legs that are too short may be unable to bond to the surface reliably, legs that are too long may be too flexible, adding to the positional uncertainty of the tip atoms during a mechanosynthetic operation. Where issues such as surface functionalization and lattice mismatches are not issues, legs can be very short (e.g., a single oxygen atom could serve as each leg).

With respect to the number of legs, the examples provided depict tips with three legs. This helps provide stability for reactions which require the application of force to the tip. Tips with less than three legs, or more than three legs, or tips where not all of the linkers have bound to the surface, could also be used as long as the required stability is provided. On a tip with multiple legs, each leg does not need to be identical.

Legs may incorporate linkers (if not, the leg may be considered to also be the linker, or vice versa), which serve to provide a bridge between the rest of the leg and the body or surface. The advantage of linkers is in providing an appropriate chemistry with which to bind a surface. For example, if the rest of the leg does not have the necessary reactivity or bond strength with a surface, a linker may address the issue, as demonstrated with the exemplary O, NH, and S linkers in the examples herein. Linkers may also be used to adjust the geometry of the legs, for example, helping them to fit the surface lattice spacing better, or adjusting their length or rigidity.

Feedstock serves as a source of atoms which can be added to a workpiece. Feedstock is chosen not only by what atom or atoms is contains, but by how it binds to a tip's active site and the desired location on a workpiece. There are many ways, for example, to donate carbon atoms to a workpiece, and examples using C2, CH2, and CH3 are all presented herein. Context will determine which is most appropriate, though often more than one could be used to build a given workpiece, assuming appropriate alterations in the build sequence.

The surface to which a tip is being attached has a variety of important characteristics, including chemical reactivity, surface smoothness, lattice spacing, linker-surface bond strength, and internal bond strength. In terms of chemical reactivity, the surface must bind to the linkers, but preferably no other parts of the tip. The surface's lattice spacing must allow linker binding without excessive strain. The linker-surface bond strength must suffice so that the bonds do not rupture if pulling forces are required. And, the internal (surface-surface) bonds must be of sufficient strength that, if pulling forces are required, the entire tip, along with one or more surface atoms, is not ripped from the surface.

With surface-mounted tips being broken down into the described modules, and the important functional characteristics of each module described, and realizing that this modular design at least to an extent isolates various modules from one another, facilitating module re-use and combinatorial creational of new tips, along with the examples presented herein, this provides a design paradigm for the design and synthesis of new tips that can be generalized well beyond the specific examples provided.

FIG. 1 depicts one version of an abstraction tip that may be used to remove hydrogen, among other moieties, from a workpiece. Radical 101 is used to bind the moiety to be abstracted, and serves as the tip's active site. The active site is connected to body 102, which in this example is adamantane. The body is connected to three methyl group legs, exemplified by leg 103. Each leg is connected to a sulfur linker, exemplified by linker 104. Each linker is bound to surface 105. As an abstraction tip, no feedstock is present.

Figure 2:
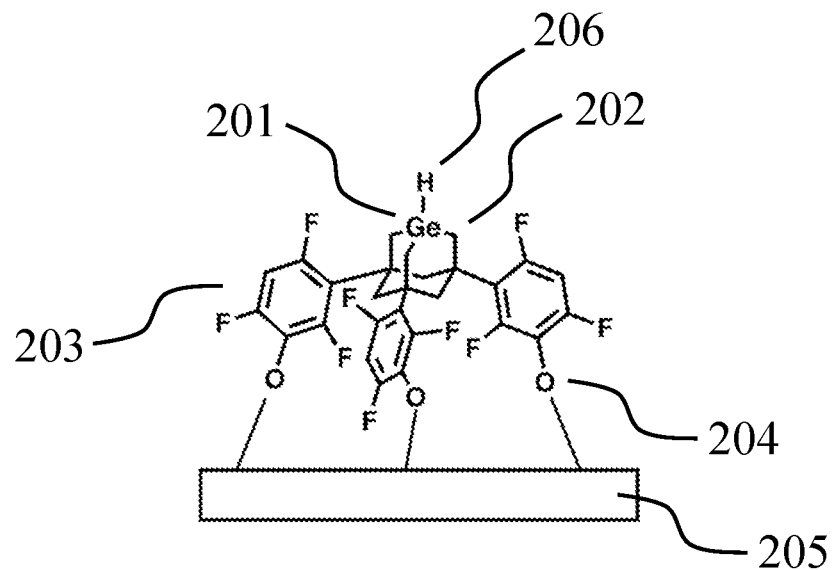
FIG. 2 depicts the modular parts of another exemplary tip.

As a different example, with feedstock, FIG. 2 depicts one version of a tip capable of donating hydrogen to many atom types. Active site 201 is a Ge atom, which in this case is part of a substituted adamantane body 202. Trifluorobenzene (which could be viewed as trifluorophenol if the linkers were considered to be part of this structure) legs are used, exemplified by leg 203, and each leg is connected to an oxygen linker 204, which connects to surface 205. Feedstock 206 is connected to active site 201.

Exemplary Tips

Surface-mounted tips, along with their routes of synthesis, have been devised which carry out mechanosynthetic reactions while minimizing or eliminating issues such as tip dimerization and improper tip orientation during surface mounting, and allow for proper leg length and flexibility and proper linker chemistry to bind to the exemplary surfaces. These synthetic routes allow for the bulk manufacture of many diverse tip types, thereby facilitating many different mechanosynthetic reactions while having the benefits described for surface-mounted tips and the processes for using such tips.

The set of tips described includes an abstraction tip with a C2-based active site (capable of extracting many atoms from many different types of workpieces, including, e.g., hydrogen from diamond), a hydrogen donation tip, a C2 donation tip, a Methyl donation tip, and a donation tip which can donate SiH3, GeH3, Si(CH3)3, or Ge(CH3)3, depending on the feedstock attached to the Ge active atom in its substituted adamantane body.

To demonstrate the modular design described herein, various versions of each tip are depicted. Specially, each tip is shown with three trifluorobenzene legs which can be linked to either a chlorinated silicon surface, or partially-hydrogenated partially-chlorinated silicon surface, via an oxygen linker or an NH linker. A version of each tip is also depicted where the legs are methyl groups, using sulfur linkers to connect to an Au surface. These various versions provide for a variety of surface properties and surface attachment chemistries and demonstrate how a body can be used to isolate an active site from other changes in the tip, as the tips continue to function as desired after changing the legs, linkers, and surface.

Note that a silicon surface has stronger intra-surface bonds than a gold surface. When placing tips on a gold surface, reactions that require substantial pulling forces (exceeding a few nN) may pull the tip from the surface (taking one or more gold atoms with it), or cause the tip to slide sideways across the surface. Nonetheless, the thiol linker chemistry is very accessible, making gold a useful surface (along with lead and other similar materials) if reactions with substantial pulling forces are not required.

Figure 3:
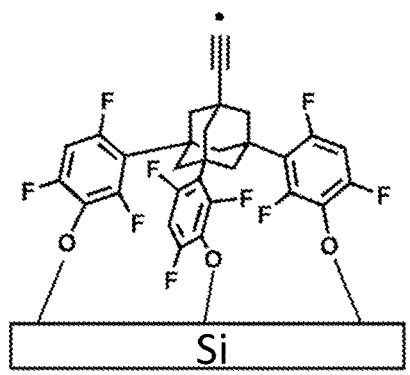
FIG. 3 depicts the AbstractO tip surface-mounted on Silicon.
Figure 4:
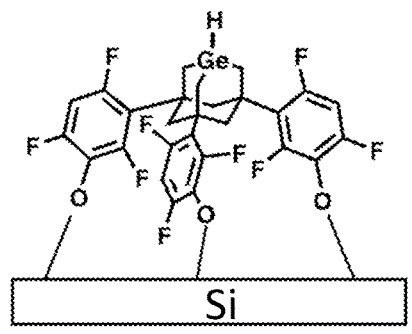
FIG. 4 depicts the HDonationO tip surface-mounted on Silicon.
Figure 5:
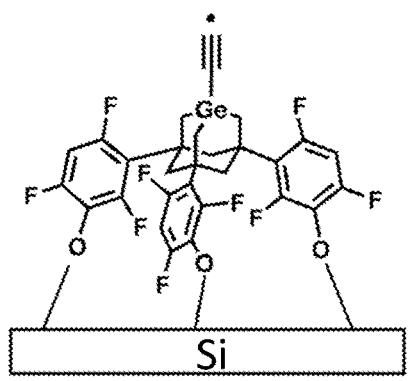
FIG. 5 depicts the C2DonationO tip surface-mounted on Silicon.
Figure 6:
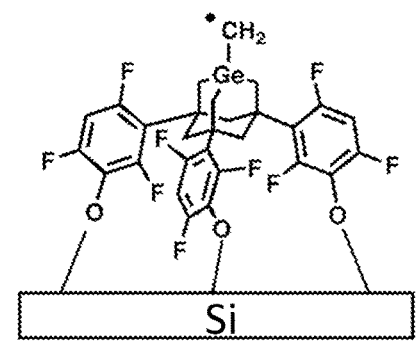
FIG. 6 depicts the MeDonationO tip surface-mounted on Silicon.
Figure 7:
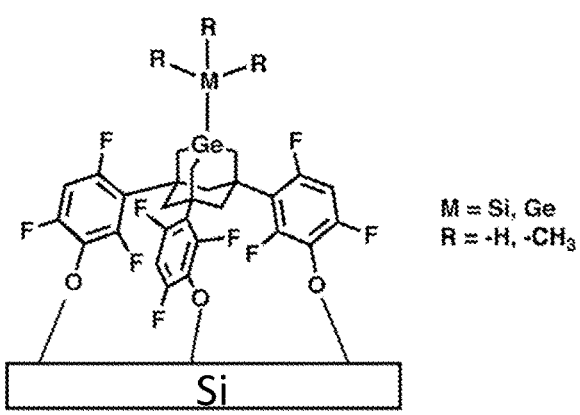
FIG. 7 depicts a tip surface-mounted on Silicon which can be SiH3DonationO, GeH3DonationO, SiMe3DonationO or GeMe3DonationO.
Figure 8:
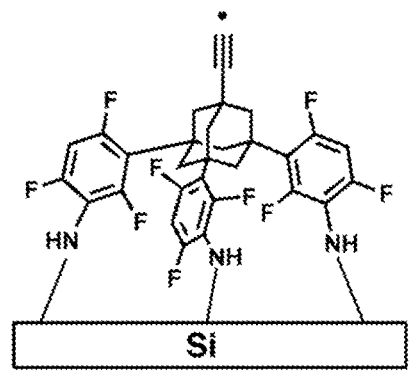
FIG. 8 depicts the AbstractNH tip surface-mounted on Silicon.
Figure 9:
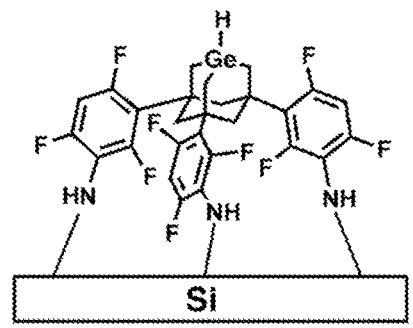
FIG. 9 depicts the HDonationNH tip surface-mounted on Silicon.
Figure 10:
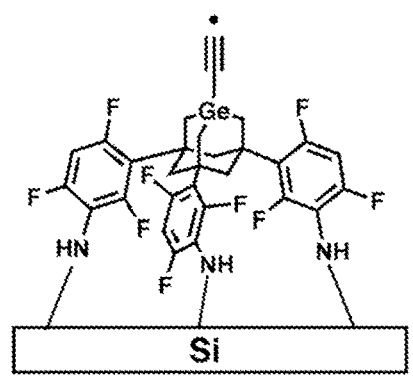
FIG. 10 depicts the C2DonationNH tip surface-mounted on Silicon.
Figure 11:
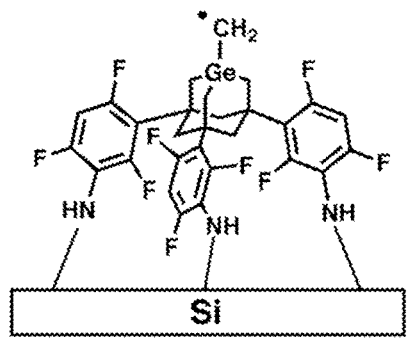
FIG. 11 depicts the MeDonationNH tip surface-mounted on Silicon.
Figure 12:
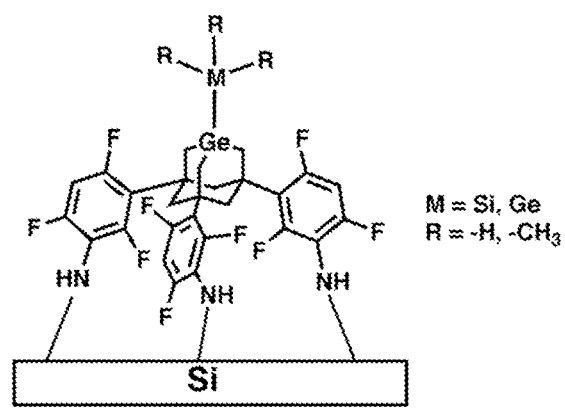
FIG. 12 depicts a tip surface-mounted on Silicon which can be SiH3DonationNH, GeH3DonationNH, SiMe3DonationNH or GeMe3DonationNH.
Figure 13:
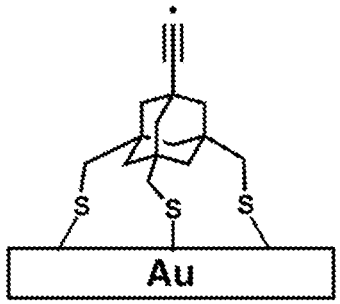
FIG. 13 depicts the AbstractS tip surface-mounted on Gold.
Figure 14:
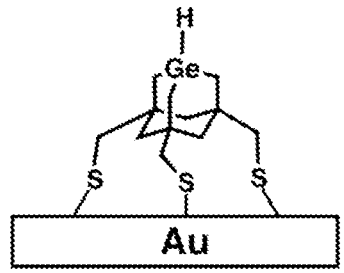
FIG. 14 depicts the HDonationS tip surface-mounted on Gold.
Figure 15:
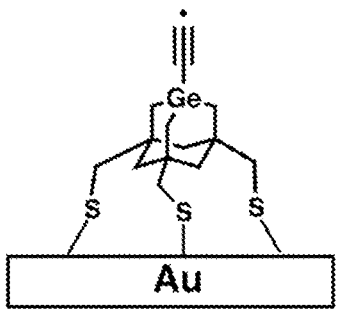
FIG. 15 depicts the C2DonationS tip surface-mounted on Gold.
Figure 16:
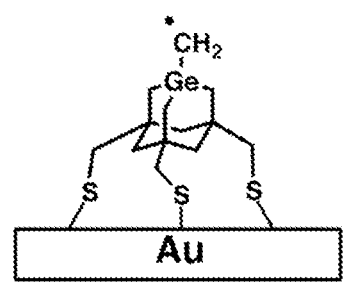
FIG. 16 depicts the MeDonationS tip surface-mounted on Gold.
Figure 17:
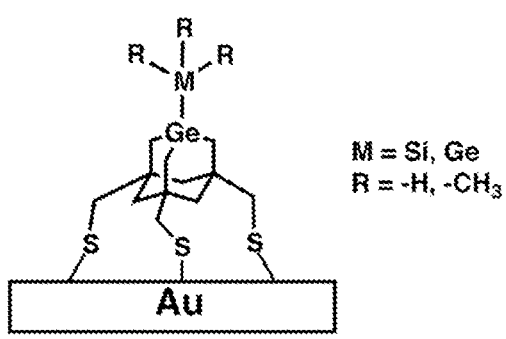
FIG. 17 depicts a tip surface-mounted on Silicon which can be SiH3DonationS, GeH3DonationS, SiMe3DonationS or GeMe3DonationS.

Each exemplary tip is shown in detail, bonded to an appropriate surface for the linker chemistry depicted, in FIGS. 3-17. FIGS. 3-7 all depict tips that use trifluorobenezene legs and oxygen linkers on a silicon surface. Specifically: FIG. 3 depicts an abstraction tip having a C2-radical-based active site, an adamantane body, trifluorobenzene legs, and oxygen linkers, on a silicon surface (all Si surfaces include, e.g., chlorinated, partially-chlorinated, and partially-hydrogenated, partially-chlorinated Si). This tip will be referred to as AbstractO. FIG. 4 depicts a hydrogen donation tip with hydrogen feedstock, a Ge-based active site incorporated into a substituted adamantane body, trifluorobenzene legs, and oxygen linkers, on a silicon surface. This tip will be referred to as HDonationO. FIG. 5 depicts a C2 donation tip with .C2 feedstock, and otherwise the same structure as FIG. 4. This tip will be referred to as C2DonationO. FIG. 6 depicts a methyl donation tip with .CH2 feedstock, and otherwise the same structure as FIG. 4. This tip will be referred to as MeDonationO. FIG. 7 depicts a donation tip that can be used to donate a variety of feedstock moieties depending on the identity of the M and R groups. M can be Si or Ge, and R can be H or CH3, allowing the tip to donate SiH3, GeH3, Si(CH3)3 or Ge(CH3)3. These tips will be referred to, respectively, as SiH3DonationO, GeH3DonationO, SiMe3DonationO, and GeMe3DonationO. FIG. 7 has otherwise the same structure as FIG. 4

FIGS. 8-12 depict tips with the same feedstock (if present), active site, bodies, and legs as FIGS. 3-7, respectively, but each tip in FIGS. 8-12 uses NH linkers instead of oxygen linkers to connect to a silicon surface. These tips will be referred to, respectively, as AbstractionNH, HDonationNH, C2DonationNH, MeDonationNH, and for the various versions of FIG. 12, SiH3DonationNH, GeH3DonationNH, SiMe3DonationNH, and GeMe3DonationNH.

FIGS. 13-17 depict tips with the same feedstock (if present), active site, and bodies as FIGS. 3-7, respectively, but each tip in FIGS. 13-17 uses methyl legs and a sulfur atom linker to connect the tip to a gold surface. These tips will be referred to, respectively, as AbstractionS, HDonationS, C2DonationS, MeDonationS, and for the various versions of FIG. 17, SiH3DonationS, GeH3DonationS, SiMe3DonationS, and GeMe3DonationS.

In addition to the use of these tips in their charged state, some tips could be used in their uncharged state. For example, several of the tips, such as the hydrogen donation tip, have a Ge radical active site in their discharged state. This can actually be a useful tip itself, for example, to break into a C=C bond.

Tip Synthesis

Exemplary synthetic pathways for each tip are depicted in FIGS. 18-41. Note that multiple synthetic pathways for the tip depicted in FIGS. 7, 12 and 17 due to the various possible combinations of M and R. Tips with radicals in their active form are synthesized with a protective cap. Procedures for cap removal are described herein.

Figure 18:
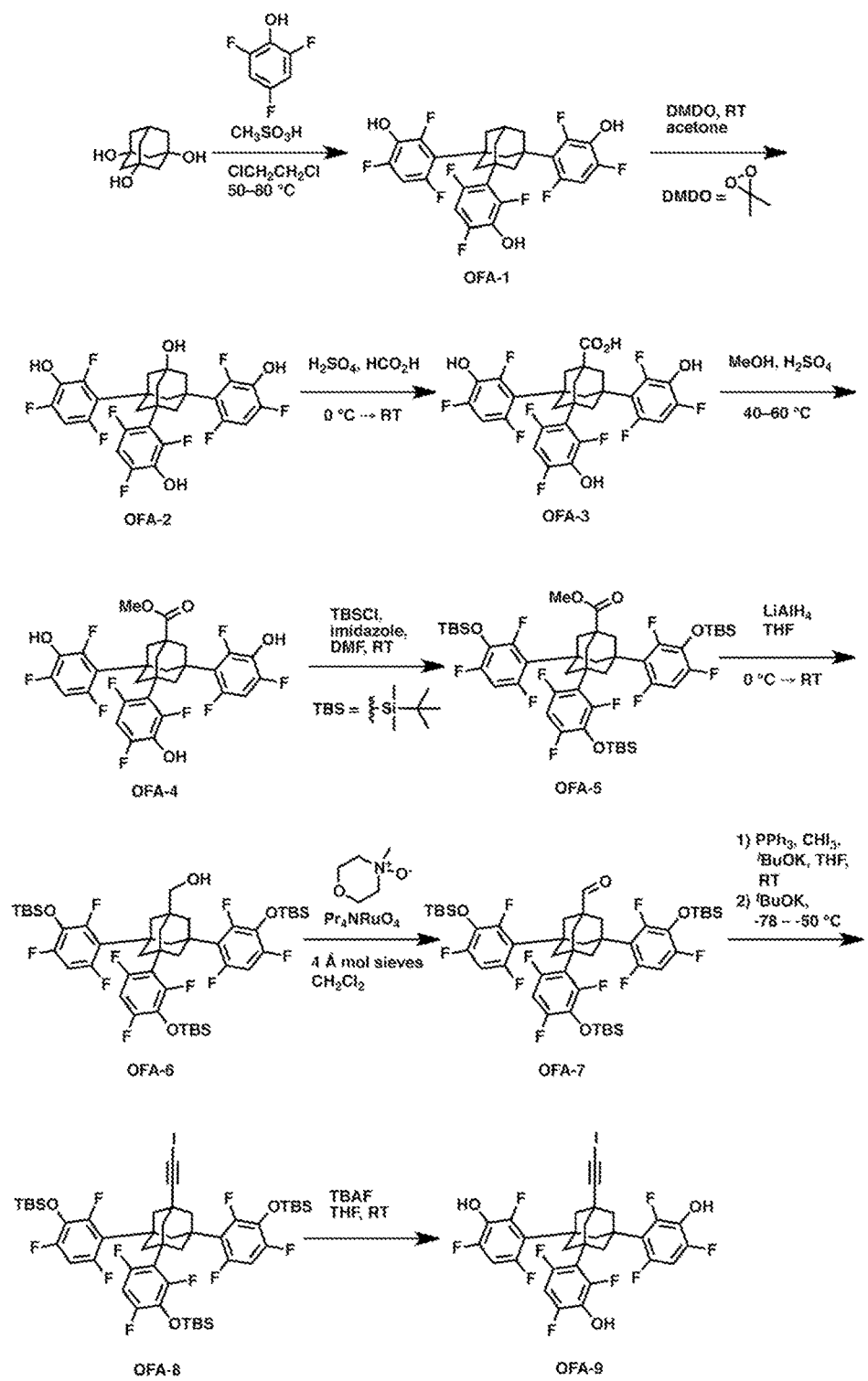
FIG. 18 depicts a synthetic route for the AbstractO tip.

FIG. 18 depicts a synthetic pathway for AbstractO. The synthesis steps are as follows: Commercially available 1,3,5-trihydroxyadamantane reacts with 2,4,6-trifluorophenol while heated between 50-80° C. under acidic conditions to give OFA-1. Treating OFA-1 with an excess dimethyldioxirane (DMDO) in acetone at room temperature selectively oxidizes the tertiary C—H bond to give alcohol OFA-2. Using Koch-Haaf conditions (Stetter, H., Schwarz, M., Hirschhorn, A. Chem. Ber. 1959, 92, 1629-1635), CO is formed from the dehydration of formic acid by concentrated sulfuric acid between −5-0° C. The CO forms a bond with the tertiary carbocation formed from the dehydration of the bridgehead alcohol at room temperature. Upon aqueous workup the carboxylic acid OFA-3 is obtained. Esterification of the carboxylic acid OFA-3 with dry methanol and catalytic sulfuric acid between 40-60° C. yields the methyl ester OFA-4. The phenolic —OH groups in OFA-4 are protected with tert-butyldimethylsilyl chloride (TBSCl) in the presence of imidazole at room temperature to give the TBS-silyl ether OFA-5. Reduction of the methyl ester with LiAlH4 in tetrahydrofuran (THF) between 0° C. and room temperature gives the methyl alcohol OFA-6. Oxidation of the methyl alcohol to the aldehyde OFA-7 proceeds with catalytic tetrapropylammonium perruthenate ((Pr4N)RuO4, TPAP) and stoichiometric N-methylmorpholine-N-oxide (NMO). The presence of 4 Å powdered molecular sieves in the reaction mixture adsorbs any water present and decreases the probability of over-oxidation to the carboxylic acid (Ley, S. V., Norman, J., Griffith, W. P., Marsden, S. P., Synthesis, 1994, 639-666). Using a modified Corey-Fuchs procedure (Michel, P., Rassat, A. Tetrahedron Lett. 1999, 40, 8570-8581), the aldehyde in THF is added to a premixed solution of iodoform (CHI3), triphenylphosphine, and potassium tert-butoxide at room temperature in THF to undergo a carbon-carbon bond forming reaction to give the 1,1-diiodoalkene. Single elimination of the vinyl iodide with excess potassium tert-butoxide and careful temperature control (−78° C.-−50° C.) yields the iodoalkyne OFA-8. It is possible to form the terminal alkyne from this reaction if temperature is not carefully controlled, however, the terminal alkyne can be iodinated with N-iodosuccinimide/AgNO3 or, alternatively, with I2 in basic methanol. The final global deprotection of the TBS-silyl ether groups is performed with tetra-n-butylammonium fluoride (TBAF). Upon aqueous workup, the AbstractO tip with free phenol linkers OFA-9 is obtained.

Figure 19:
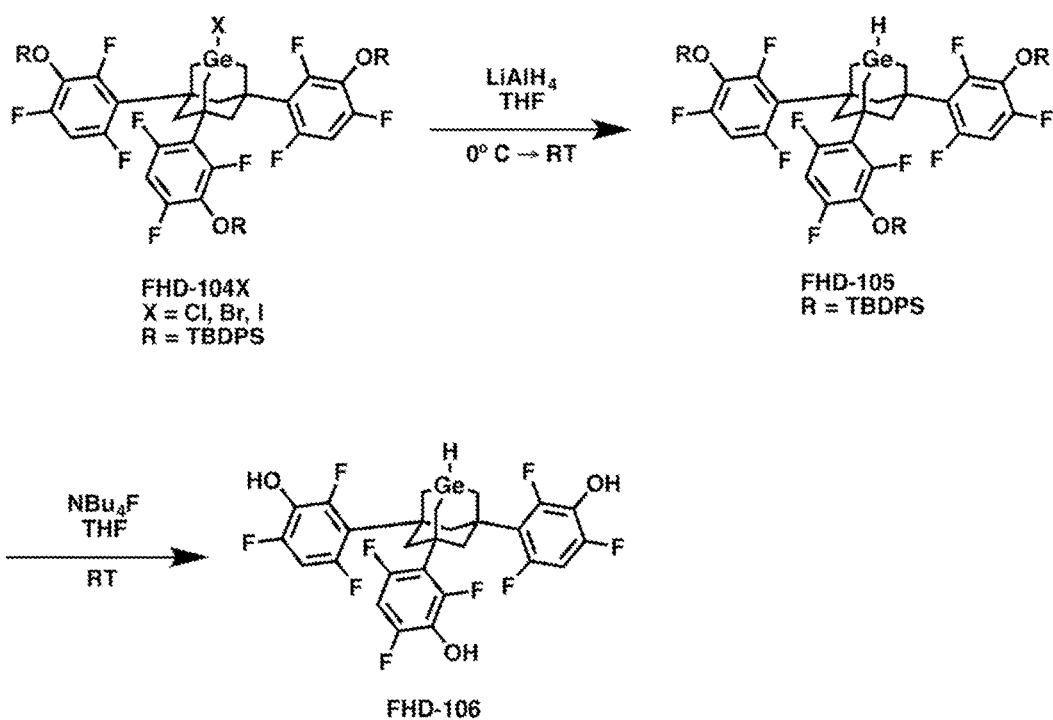
FIG. 19 depicts a synthetic route for the HDonationO tip.

FIG. 19 depicts a synthetic pathway for HDonationO. The synthesis steps are as follows: FHD-104X is reduced by excess lithium aluminum hydride in THF solvent at 0° C., converting the germanium halide to the germanium hydride FHD-105. Tetra-n-butylammonium fluoride is used to deprotect the tert-butyldimethylsilyl protecting groups from FHD-105 in THF to yield the triphenol FHD-106, the HdonationOHtip.

Figure 20:
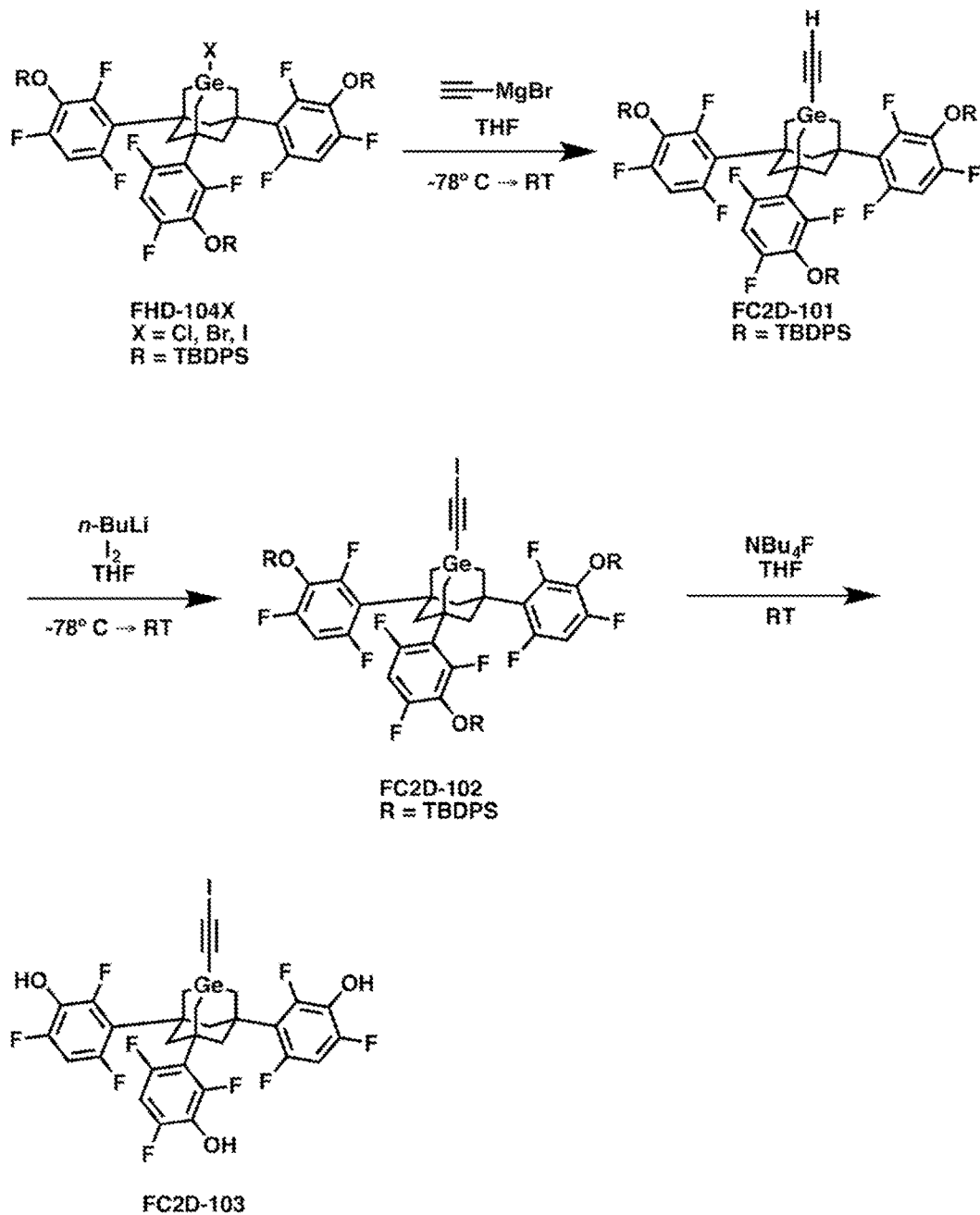
FIG. 20 depicts a synthetic route for the C2DonationO tip.

FIG. 20 depicts a synthetic pathway for C2DonationO. The synthesis steps are as follows: The Grignard reagent ethynylmagnesium bromide in THF solution is added to FHD-104X dissolved in dry THF and cooled to −78 C dropwise with rapid stirring. The reaction is stirred for 1 hour, warmed to 0 C for 1 hour, and stirred for 1 hour at room temperature to form FC2D-101. FC2D-101 is dissolved in dry THF and cooled to −78 C. A solution of n-butyllithium in hexanes is added and the reaction is stirred for 1 hour at −78 C. A solution of iodine in dry THF is added and the reaction is allowed to warm to room temperature to yield FC2D-102. FC2D-102 is dissolved in THF and stirred rapidly at room temperature. Tetra-n-butylammonium fluoride is added and the reaction is stirred for 1 hour to yield FC2D-103, the C2DonationO tip.

Figure 21:
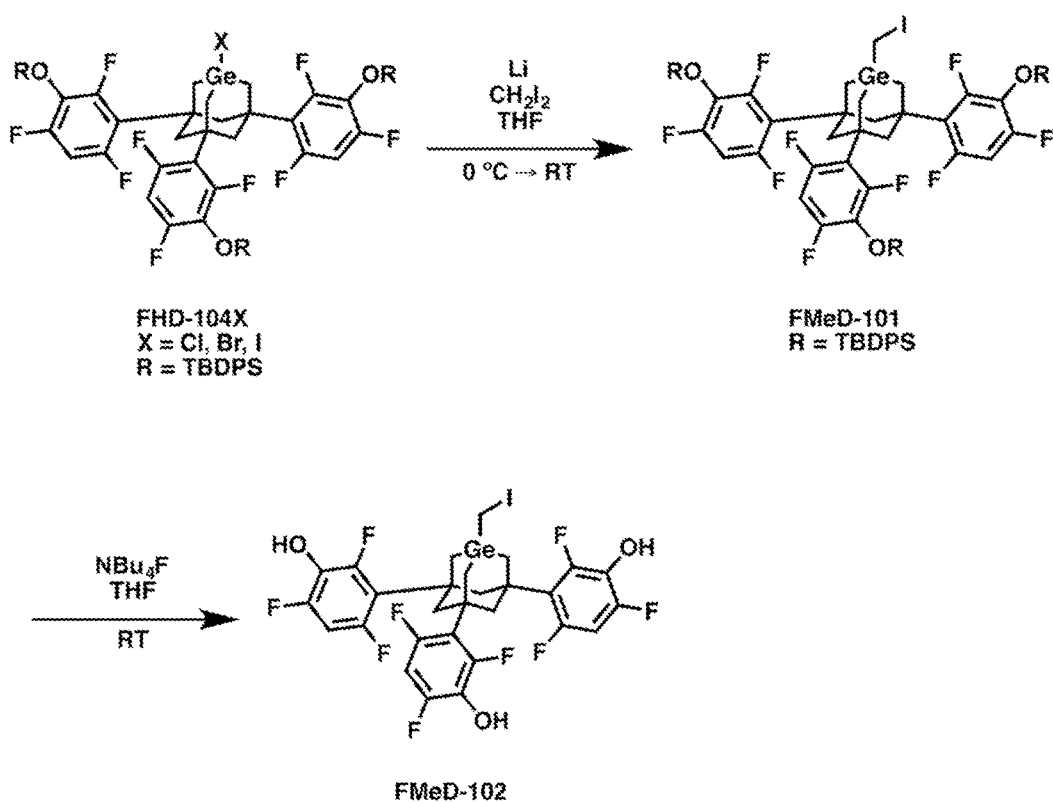
FIG. 21 depicts a synthetic route for the MeDonationO tip.

FIG. 21 depicts a synthetic pathway for MeDonationO. The synthesis steps are as follows: The germanium halide FHD-104X in THF solution is reduced with lithium metal to generate a lithiated germanium species in situ. The solution is then slowly added dropwise to a solution of 10-fold excess methylene iodide (CH2I2) in THF cooled to 0 C. This method of addition favors the formation iodomethyl germane FMeD-101 over methylene-bridged germanes. Stoichiometric tetra-n-butylammonium fluoride is used to deprotect the tert-butyldimethylsilyl protecting groups from FMeD-101 in THF to yield the triphenol FMeD-102, the MeDonationO tip.

Figure 22:
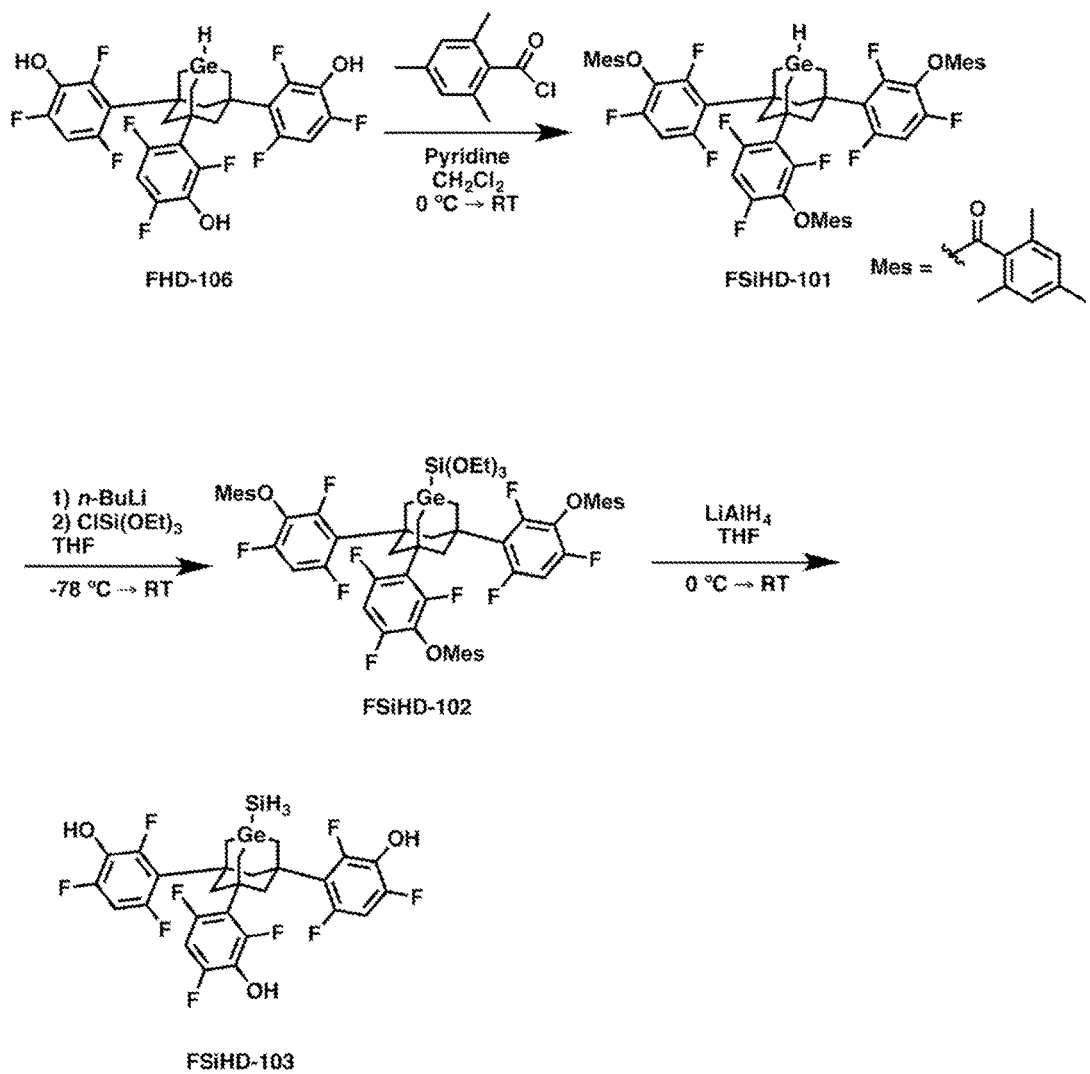
FIG. 22 depicts a synthetic route for the SiH3DonationO tip.

FIG. 22 depicts a synthetic pathway for SiH3DonationO. The synthesis steps are as follows: The phenols of FHD-106 are acylated with mesitoyl chloride in dichloromethane with pyridine base. (Corey et al., JACS 1969, 91, 4398) The mesitoate protecting group is utilized due to its stability to the lithiation conditions necessary for FSiHD-102. FSiHD-101 in dry THF solution is deprotonated with n-butyllithium in hexanes at −78 C and slowly warmed to room temperature. The resulting lithiated anion is silylated with chlorotriethoxysilane in THF solution to yield FSiHD-102. FSiHD-102 in dry THF solution is cooled to 0 C and lithium aluminum hydride in THF solution is added to cleave the mesitoate esters and reduce the triethoxysilyl group, yielding FSiHD-103, the SiH3DonationO tip.

Figure 23:
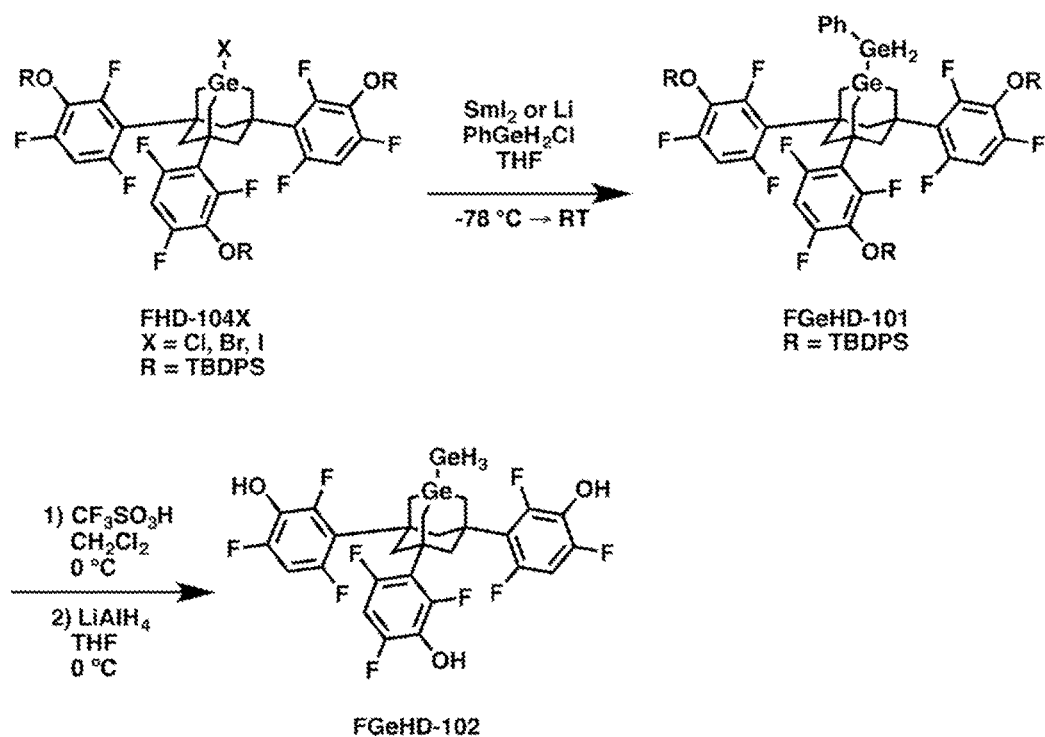
FIG. 23 depicts a synthetic route for the GeH3DonationO tip.

FIG. 23 depicts a synthetic pathway for GeH3DonationO. The synthesis steps are as follows: To form FGeHD-101, the germanium halide FHD-104X in THF solution is reduced with lithium metal to generate a lithiated germanium species in situ. The solution is then removed by syringe to separate the lithiated germanium species from the unreacted lithium metal and then slowly added dropwise to a solution of chloro(phenyl)germane (Ohshita, J.; Toyoshima, Y.; Iwata, A.; Tang, H.; Kunai, A. Chem. Lett. 2001, 886-887) in THF cooled to 0 C. It is necessary to separate the lithiated germanium species from excess lithium metal before addition to the trimethylgermanium chloride because lithium is capable of exchange reactions with germanium halides. FGeHD-101 is dephenylated with trifluoromethanesufonic acid in dichloromethane at 0 C. The crude reaction isolate after neutralization and workup is then dissolved in dry THF. The reaction is cooled to 0 C and lithium aluminum hydride is added dropwise to produce the germane FGeHD-102, the GeH3DonationO tip.

Figure 24:
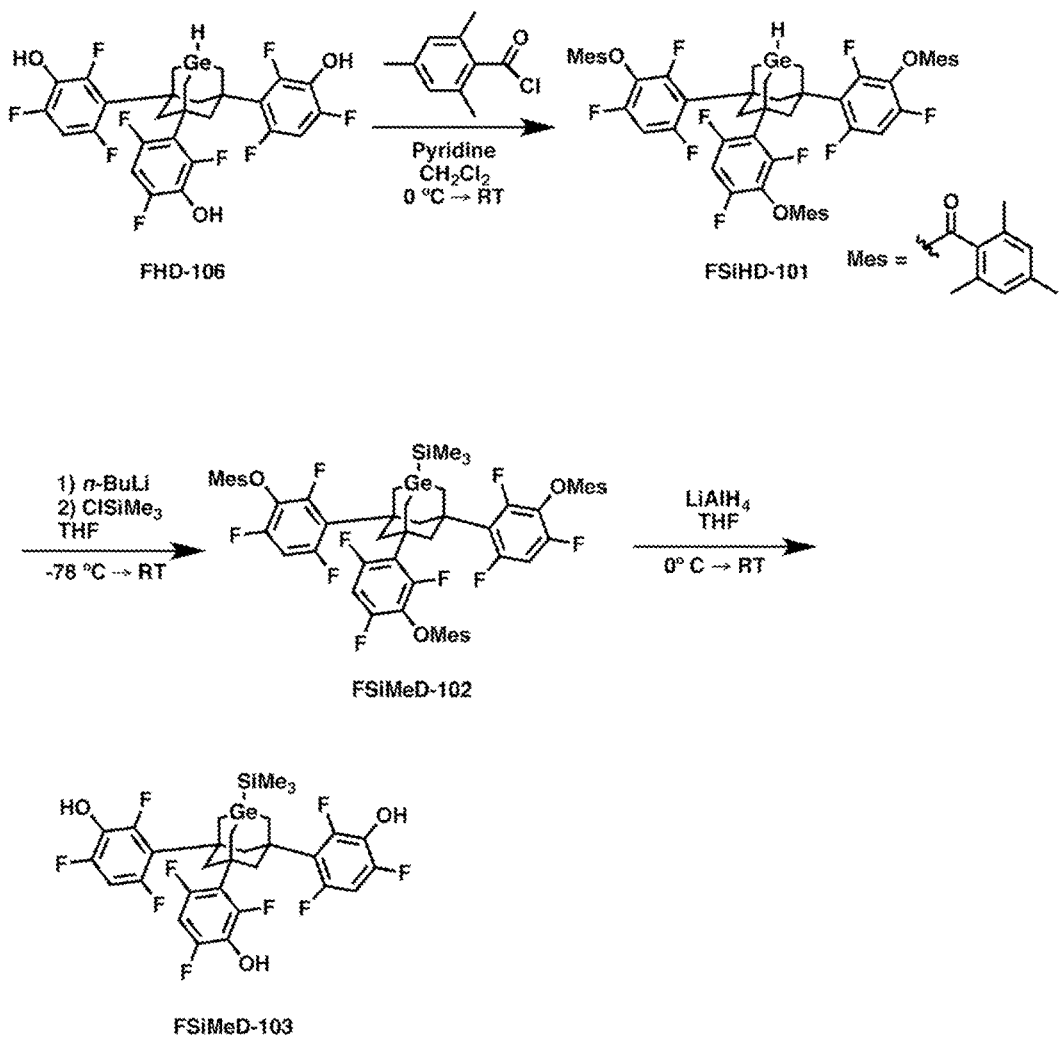
FIG. 24 depicts a synthetic route for the SiMe3DonationO tip.

FIG. 24 depicts a synthetic pathway for SiMe3DonationO. The synthesis steps are as follows: To prepare FSiHD-101, the phenols of FHD-106 are acylated with mesitoyl chloride in dichloromethane with pyridine base. (Corey et al., JACS 1969, 91, 4398) The mesitoate protecting group is utilized due to its stability to the lithiation conditions necessary for FSiHD-102. FSiHD-101 in dry THF solution is deprotonated with n-butyllithium in hexanes at −78 C and slowly warmed to room temperature. The resulting lithiated anion is silylated with trimethylsilyl chloride in THF solution to yield FSiMeD-102. FSiMeD-102 in dry THF solution is cooled to 0 C and lithium aluminum hydride in THF solution is added to cleave the mesitoate esters, yielding FSiMeD-103, the SiMe3DonationO tip.

Figure 25:
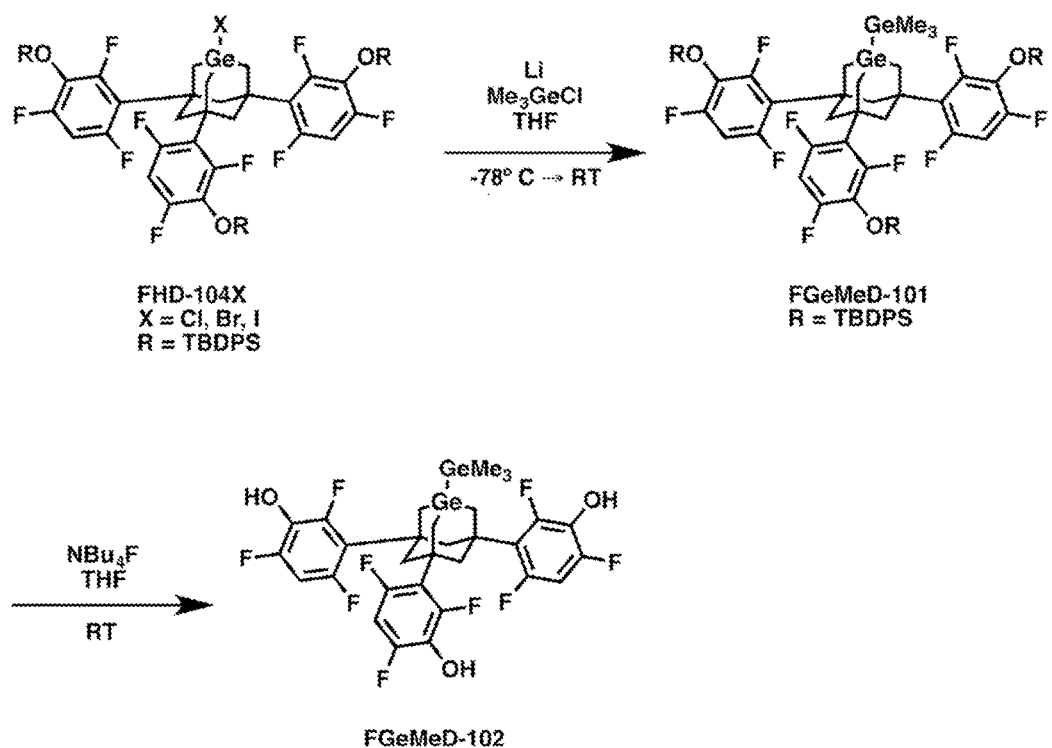
FIG. 25 depicts a synthetic route for the GeMe3DonationO tip.

FIG. 25 depicts a synthetic pathway for GeMe3DonationO. The synthesis steps are as follows: To prepare FGeMeD-101, the germanium halide FHD-104X in THF solution is reduced with lithium metal to generate a lithiated germanium species in situ. The solution is then removed by syringe to separate the lithiated germanium species from the unreacted lithium metal and then slowly added dropwise to a solution of trimethylgermanium chloride in THF cooled to 0 C. It is necessary to separate the lithiated germanium species from excess lithium metal before addition to the trimethylgermanium chloride because lithium is capable of exchange reactions with germanium halides. Stoichiometric tetra-n-butylammonium fluoride is used to deprotect the tert-butyldimethylsilyl protecting groups from FMeD-101 in THF to yield the triphenol FGeMeD-102, the GeMe3DonationO tip.

Figure 26:
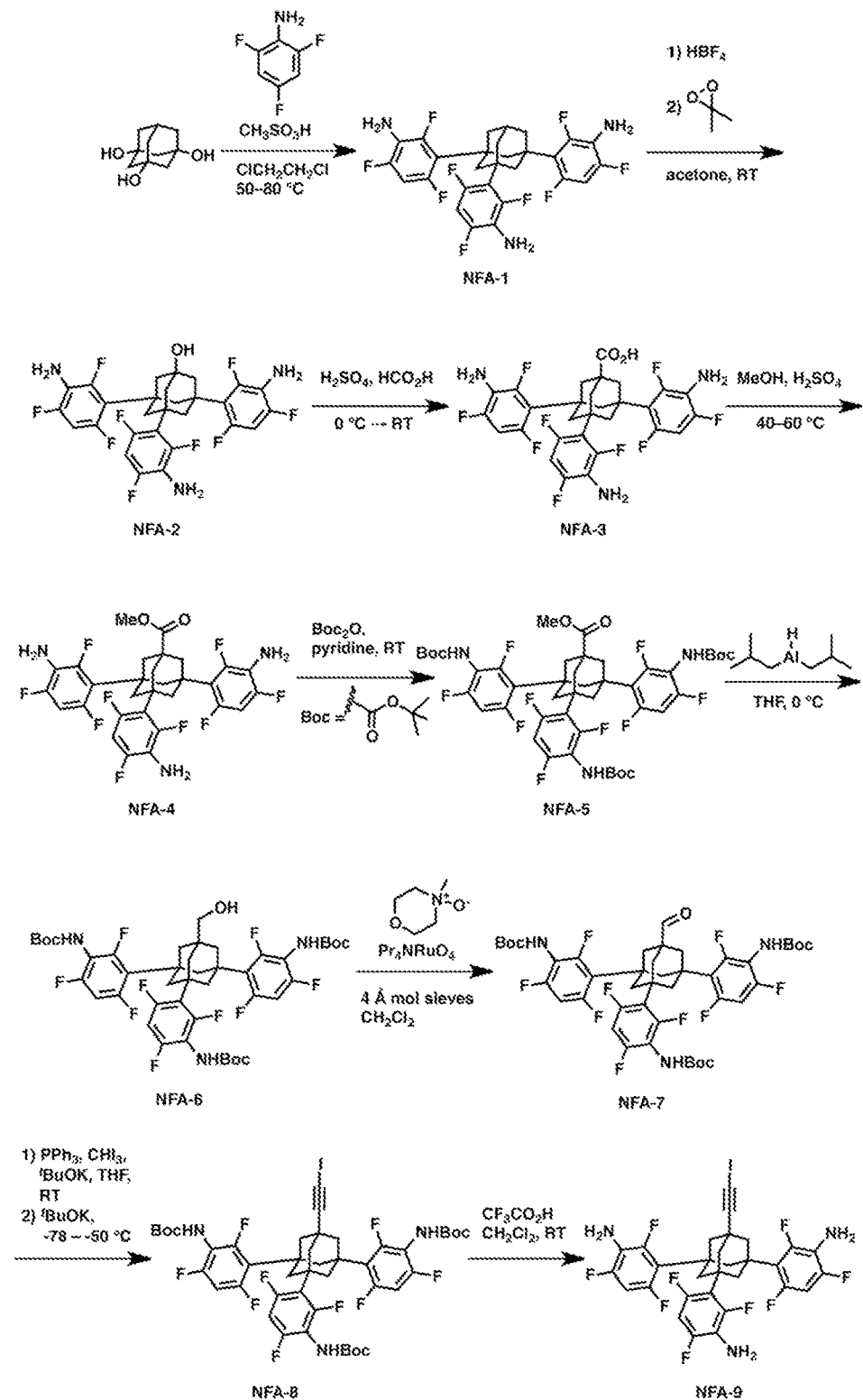
FIG. 26 depicts a synthetic route for the AbstractNH tip.

FIG. 26 depicts a synthetic pathway for AbstractNH. The synthesis steps are as follows: Commercially available 1,3,5-trihydroxyadamantane reacts with 2,4,6-trifluoroaniline while heated to 50-80° C. under acidic conditions in 1,2-dichloroethane to give NFA-1. Treating NFA-1 tetrafluoroboric acid forms the tetrafluoroborate amine salt in situ to prevent oxidation of the amines. (Asencio, G., Gonzalez-Nuñez, M. E., Bernardini, C. B., Mello, R., Adam, W. J. Am. Chem. Soc., 1993, 115, 7250-7253) Following the salt formation, an excess of dimethyldioxirane (DMDO) in acetone at room temperature selectively oxidizes the tertiary C—H bond to give alcohol NFA-2. Using Koch-Haaf conditions (Stetter, H., Schwarz, M., Hirschhorn, A. Chem. Ber. 1959, 92, 1629-1635), CO is formed from the dehydration of formic acid by concentrated sulfuric acid. The CO forms a bond with the tertiary carbocation formed from the dehydration of the bridgehead alcohol. Upon aqueous workup the carboxylic acid NFA-3 is obtained. Esterification of NFA-3 with dry methanol and catalytic sulfuric acid yields the ester NFA-4 that can be reduced readily with diisobutylaluminum hydride. Di-tert-butyl-dicarbonate (Boc2O) is used to protect the —NH2 groups and to be removable by acid hydrolysis. Treating NFA-4 with Boc2O yields the protected compound NFA-5. Reduction of the methyl ester with LiAlH4 in tetrahydrofuran (THF) gives the methyl alcohol NFA-6. Oxidation of the methyl alcohol to the aldehyde NFA-7 proceeds with catalytic tetrapropylammonium perruthenate (TPAP) and stoichiometric N-methylmorpholine- N-oxide (NMO). The presence of 4 Å powdered molecular sieves in the reaction mixture adsorbs any water present and decreases the probability of over-oxidation to the carboxylic acid. (Ley, S. V., Norman, J., Griffith, W. P., Marsden, S. P., Synthesis, 1994, 639-666) Using a modified Corey-Fuchs procedure (Michel, P., Rassat, A. Tetrahedron Lett. 1999, 40, 8570-8581), the aldehyde in THF is added to a premixed solution of iodoform (CHI3), triphenylphosphine, and potassium tert-butoxide at room temperature in THF to undergo a carbon-carbon bond forming reaction to give the 1,1-diiodoalkene. Single elimination of iodide with careful temperature (−78° to −50° C.) and excess potassium tert-butoxide control yields the iodoalkyne NFA-8. It is possible to form the terminal alkyne from this reaction if temperature is not carefully controlled, however, the terminal alkyne can be iodinated with N-iodosuccinimide/AgNO3 or, alternatively, with I2 in basic methanol. The final global deprotection of the Boc-groups is performed with trifluoroacetic acid (TFA) in dichloromethane at RT. Upon aqueous workup, NFA-9, the AbstractNH tip, is obtained.

Figure 27:
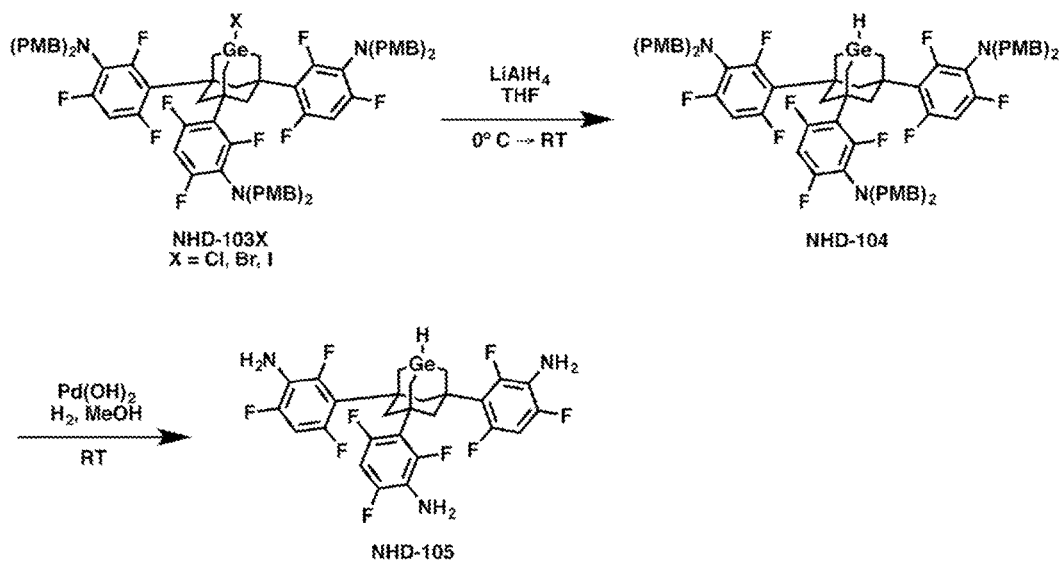
FIG. 27 depicts a synthetic route for the HDonationO tip.

FIG. 27 depicts a synthetic pathway for HDonationNH. The synthesis steps are as follows: NHD-103X in dry THF solution is cooled to 0 C and lithium aluminum hydride in THF solution is added to reduce the germanium halide, yielding NHD-104. NHD-104 is dissolved in dry MeOH and added to a reaction vessel suitable for pressurized hydrogenations. Palladium hydroxide catalyst is added and the vessel pressurized with hydrogen gas. Agitation of the reaction under the pressurized hydrogen atmosphere yields NHD-105, the HDonationNH tip.

Figure 28:
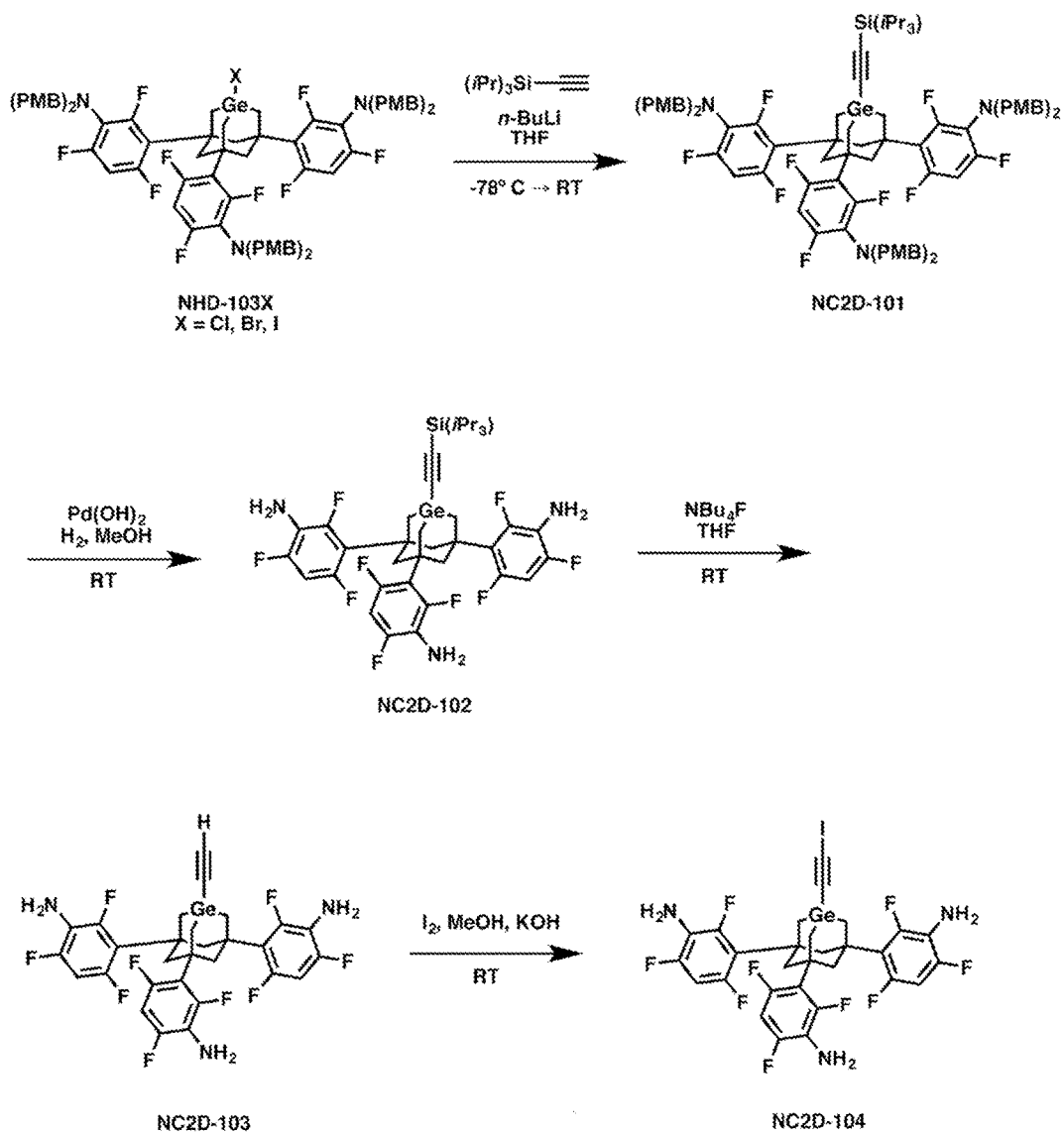
FIG. 28 depicts a synthetic route for the C2DonationO tip.

FIG. 28 depicts a synthetic pathway for C2DonationNH. The synthesis steps are as follows: (Triisopropylsilyl)acetylene is dissolved in dry THF and cooled to −78 C. n-Butyllithium solution in hexanes is slowly added dropwise to deprotonate the acetylene hydrogen. The solution is stirred for 1 hour, allowed to warm to room temperature, and is added dropwise to NHD-103X in dry THF solution cooled to −78 C. The reaction is stirred for 1 hour, warmed to 0 C for 1 hour, and stirred for 1 hour at room temperature to form NC2D-101. NC2D-101 is dissolved in dry MeOH and added to a reaction vessel suitable for pressurized hydrogenations. Palladium hydroxide catalyst is added and the vessel pressurized with hydrogen gas. Agitation of the reaction under the pressurized hydrogen atmosphere yields NC2D-102. The steric bulk of both the triisopropylsilyl group and the germaadamantane core prevent hydrogenation of the alkyne. NC2D-102 is dissolved in THF and stirred rapidly at room temperature. Tetra-n-butylammonium fluoride is added and the reaction is stirred for 1 hour at RT to yield NC2D-103. NC2D-103 is dissolved in MeOH and rapidly stirred. Potassium hydroxide is added and a solution of iodine in methanol is added slowly dropwise at RT to yield NC2D-104, the C2DonationNH tip.

Figure 29:
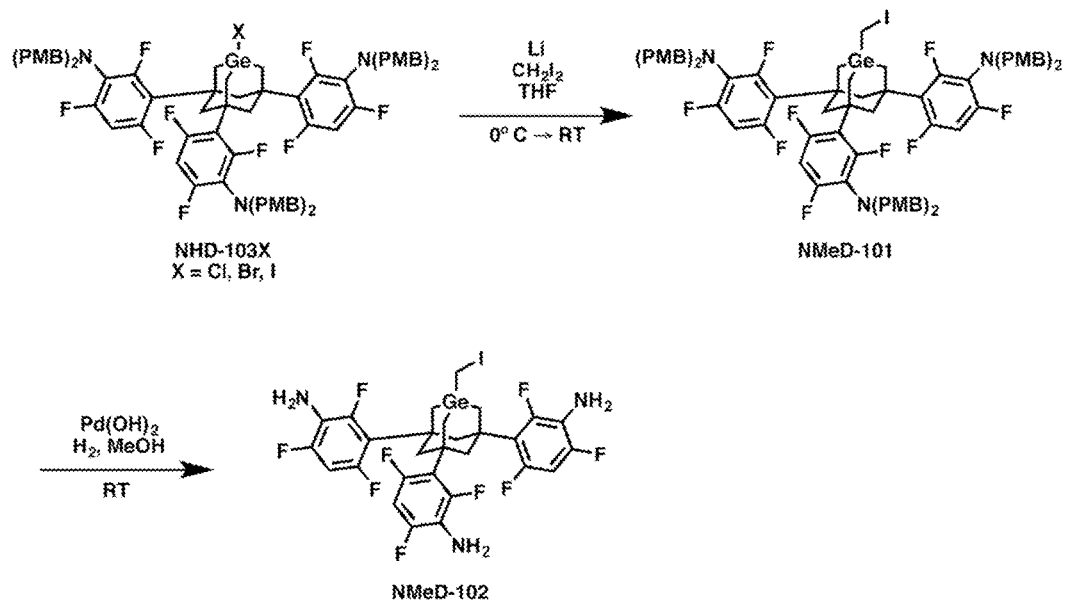
FIG. 29 depicts a synthetic route for the MeDonationO tip.

FIG. 29 depicts a synthetic pathway for MeDonationNH. The synthesis steps are as follows: The germanium halide NHD-103X in THF solution is reduced with lithium metal to generate a lithiated germanium species in situ. The solution is then slowly added dropwise to a solution of 10-fold excess methylene iodine (CH2I2) in THF cooled to 0 C. This method of addition favors the formation iodomethyl germane NMeD-101 over methylene-bridged germanes. NMeD-101 is dissolved in dry MeOH and added to a reaction vessel suitable for pressurized hydrogenations. Palladium hydroxide catalyst is added and the vessel pressurized with hydrogen gas. Agitation of the reaction under the pressurized hydrogen atmosphere yields NMeD-102, the MeDonationNH tip.

Figure 30:
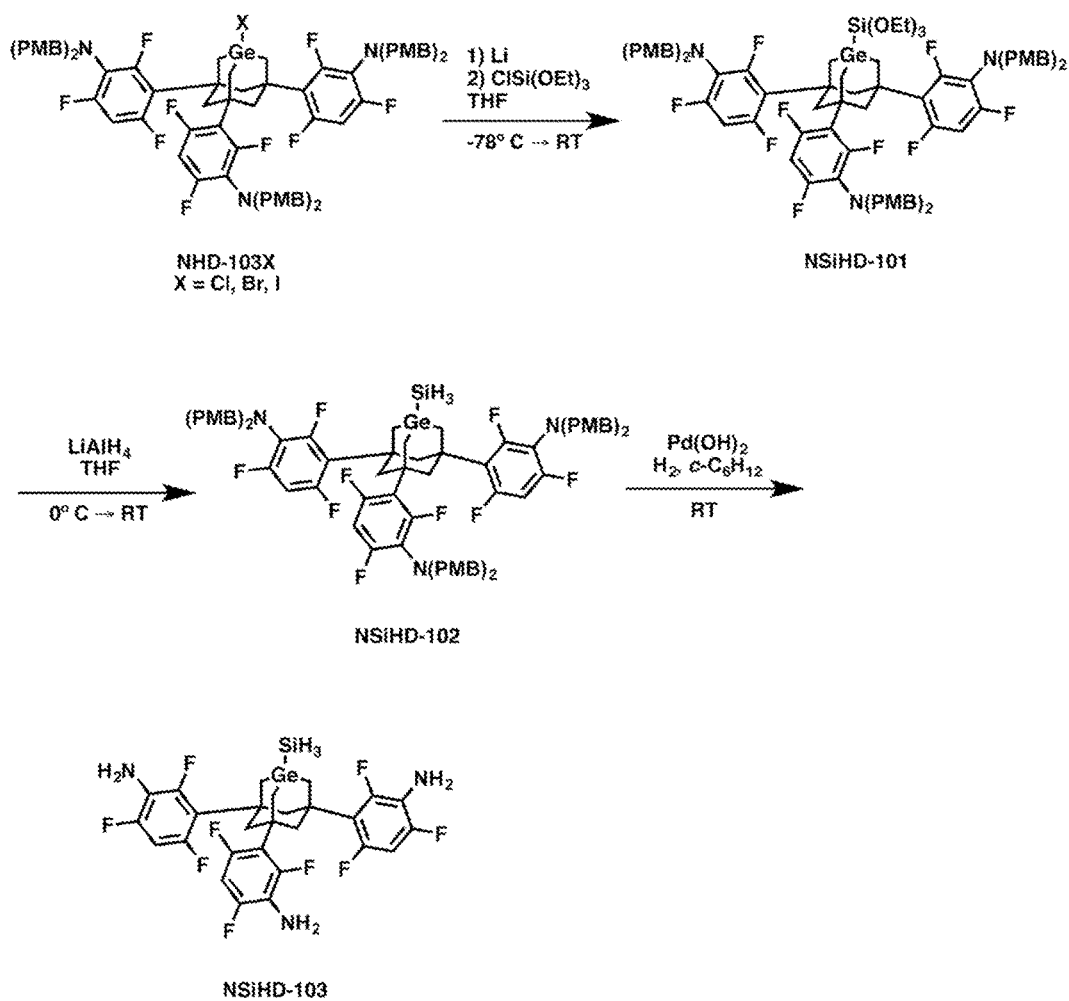
FIG. 30 depicts a synthetic route for the SiH3DonationO tip.

FIG. 30 depicts a synthetic pathway for SiH3DonationNH. The synthesis steps are as follows: The germanium halide NHD-103X in THF solution is reduced with lithium metal at −78 C to generate a lithiated germanium species in situ. The solution is then removed by syringe to separate the lithiated germanium species from the unreacted lithium metal and then slowly added dropwise to a solution of excess chlorotriethoxysilane in THF cooled to 0 C and the reaction is allowed to warm to room temperature to produce NSiHD-101. NSiHD-101 in THF solution cooled to 0 C is reduced with lithium aluminum hydride to generate NSiHD-102. NSiHD-102 is dissolved in cyclohexane and added to a reaction vessel suitable for pressurized hydrogenations. Palladium hydroxide catalyst is added and the vessel pressurized with hydrogen gas. Agitation of the reaction under the pressurized hydrogen atmosphere yields NSiHD-103, the SiH3DonationNH tip.

Figure 31:
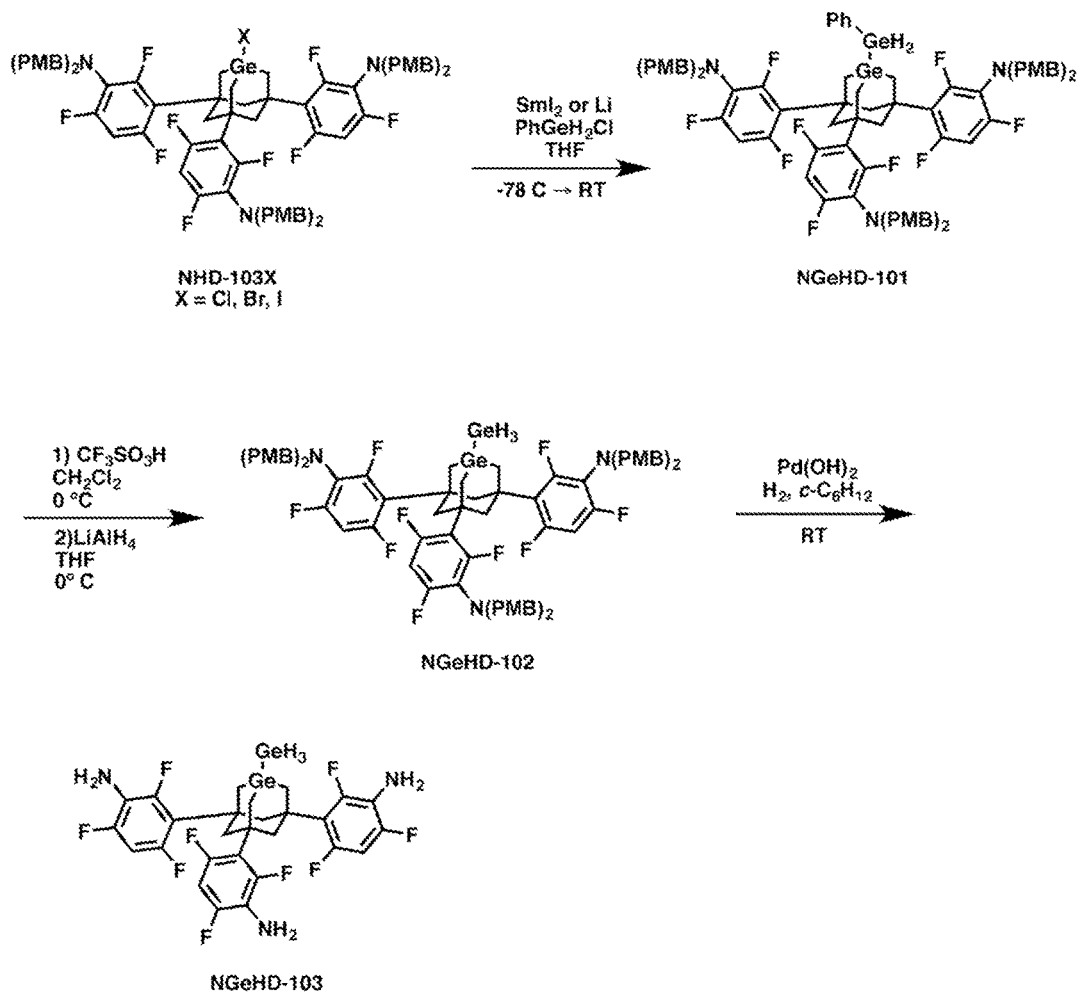
FIG. 31 depicts a synthetic route for the GeH3DonationO tip.

FIG. 31 depicts a synthetic pathway for GeH3DonationNH. The synthesis steps are as follows: The germanium halide NHD-103X in THF solution is reduced with lithium metal at −78 C to generate a lithiated germanium species in situ. The solution is then removed by syringe to separate the lithiated germanium species from the unreacted lithium metal and then slowly added dropwise to a solution of chloro(phenyl)germane in THF cooled to 0 C and the reaction is allowed to warm to room temperature to produce NGeHD-101. It is necessary to separate the lithiated germanium species from excess lithium metal before addition to the trimethylgermanium chloride to prevent lithium-halogen exchange reactivity with the chloro(phenyl)germane. NGeHD-101 is dephenylated with trifluoromethanesufonic acid at 0 C. The crude reaction isolate after neutralization of acid and workup is then dissolved in dry THF. The reaction is cooled to 0 C and lithium aluminum hydride is added to produce the germane NGeHD-102. NGeHD-102 is dissolved in cyclohexane and added to a reaction vessel suitable for pressurized hydrogenations. Palladium hydroxide catalyst is added and the vessel pressurized with hydrogen gas. Agitation of the reaction under the pressurized hydrogen atmosphere yields NGeHD-103, the GeH3DonationNH tip.

Figure 32:
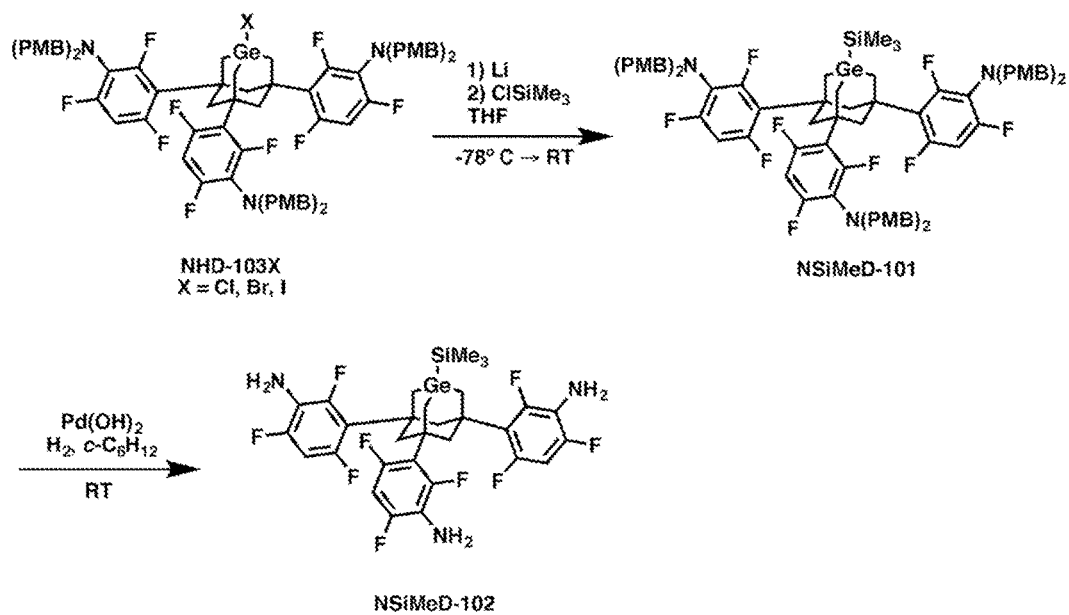
FIG. 32 depicts a synthetic route for the SiMe3DonationO tip.

FIG. 32 depicts a synthetic pathway for SiMe3DonationNH. The synthesis steps are as follows: The germanium halide NHD-103X in THF solution is reduced with lithium metal at −78 C to generate a lithiated germanium species in situ. The solution is then removed by syringe to separate the lithiated germanium species from the unreacted lithium metal and then slowly added dropwise to a solution of excess chlorotrimethylsilane in THF cooled to 0 C and the reaction is allowed to warm to room temperature to produce NSiMeD-101. NSiMeD-101 is dissolved in cyclohexane and added to a reaction vessel suitable for pressurized hydrogenations. Palladium hydroxide catalyst is added and the vessel pressurized with hydrogen gas. Agitation of the reaction under the pressurized hydrogen atmosphere yields NSiMeD-102, the SiMe3DonationNH tip.

Figure 33:
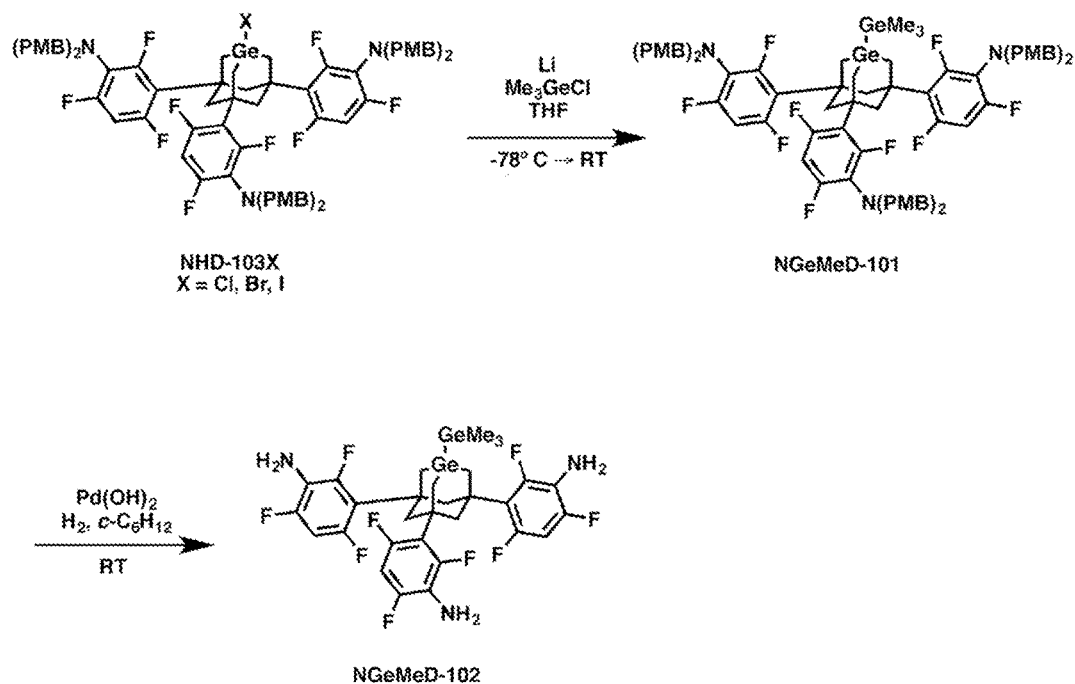
FIG. 33 depicts a synthetic route for the GeMe3DonationO tip.

FIG. 33 depicts a synthetic pathway for GeMe3DonationNH. The synthesis steps are as follows: The germanium halide NHD-103X in THF solution is reduced with lithium metal at −78 C to generate a lithiated germanium species in situ. The solution is then removed by syringe to separate the lithiated germanium species from the unreacted lithium metal and then slowly added dropwise to a solution of trimethylgermanium chloride in THF cooled to 0 C and the reaction is allowed to warm to room temperature to produce NGeMeD-101. It is necessary to separate the lithiated germanium species from excess lithium metal before addition to the trimethylgermanium chloride to prevent lithium reduction of the germanium chloride. NGeMeD-101 is dissolved in cyclohexane and added to a reaction vessel suitable for pressurized hydrogenations. Palladium hydroxide catalyst is added and the vessel pressurized with hydrogen gas. Agitation of the reaction under the pressurized hydrogen atmosphere yields NGeMeD-102, the GeMe3DonationNH tip.

Figure 34:
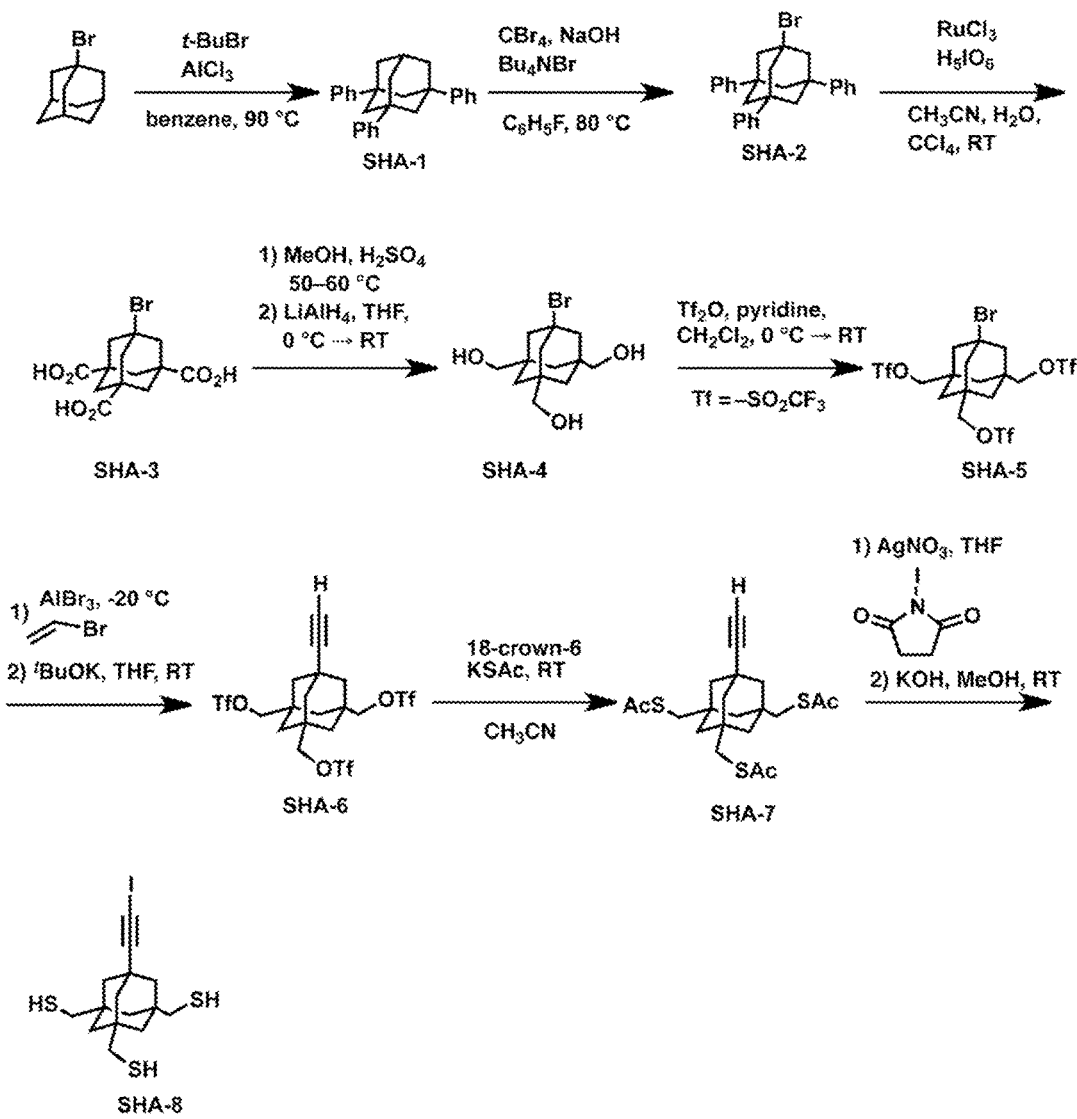
FIG. 34 depicts a synthetic route for the AbstractS tip.

FIG. 34 depicts a synthetic pathway for AbstractS. The synthesis steps are as follows: Commercially available 1-bromoadamantane undergoes a Friedel-Crafts alkylation with three separate benzene molecules under Lewis acidic conditions with AlCl3 at 90 C to yield SHA-1. Careful control of the stoichiometry of the tert-butyl bromide (2.0 equivalents) yields the 1,3,5-triphenyl adamantane (Newman, H. Synthesis, 1972, 12, 692-693). Treatment of SHA-1 in fluorobenzene and 50% aqueous NaOH solution with a phase transfer catalyst gives SHA-2. This reaction is selective at brominating the tertiary C—H bond in the adamantane (Schreiner, P. R.; Lauenstein, O.; Butova, E. D.; Gunchenko, P. A.; Kolomitsin, I. V.; Wittkopp, A.; Feder, G.; Fokin, A. A., Chem. Eur. J. 2001, 7, 4996-5003). Oxidative cleavage of the aromatic rings by RuCl3 in a biphasic mixture gives the tricarboxylic acid SHA-3 (Carlsen, P. H. J.; Katsuki, T.; Martin, V. S.; Sharpless, K. B., J. Org. Chem. 1981, 46, 3936-3938). Esterification of SHA-3 with dry methanol and catalytic sulfuric acid between 50-60° C. yields the triester SHA-4 that can be reduced readily with LiAlH4 at 0 C. The triol SHA-4 can react readily with triflic anhydride and pyridine in dichloromethane at 0 C to give the compound SHA-5. Condensing vinyl bromide at −20° C. with catalytic AlBr3 in the presence of the adamantyl bromide SHA-5 gives a dibromoethyladamantane intermediate that is used with potassium tert-butoxide to eliminate to give the alkyne SHA-6 (Malik, A. A.; Archibald, T. G.; Baum, K.; Unroe, M. R., J. Polymer Sci. Part A: Polymer Chem. 1992, 30, 1747-1754). Three equivalents of potassium thioacetate displaces the triflate groups in refluxing acetonitrile to give the compound SHA-7. The use of 18-crown-6 enhances the nucleophilicity of the thioacetate and can be added to enhance the rate of the reaction at room temperature (Kitagawa, T., Idomoto, Y.; Matsubara, H.; Hobara, D.; Kakiuchi, T.; Okazaki, T.; Komatsu, K., J. Org. Chem. 2006, 71, 1362-1369). Silver nitrate with N-iodosuccinimide in THF creates the iodoalkyne at room temperature and treatment with potassium hydroxide removes the acetate groups to give compound SHA-8, the AbstractS tip.

Figure 35:
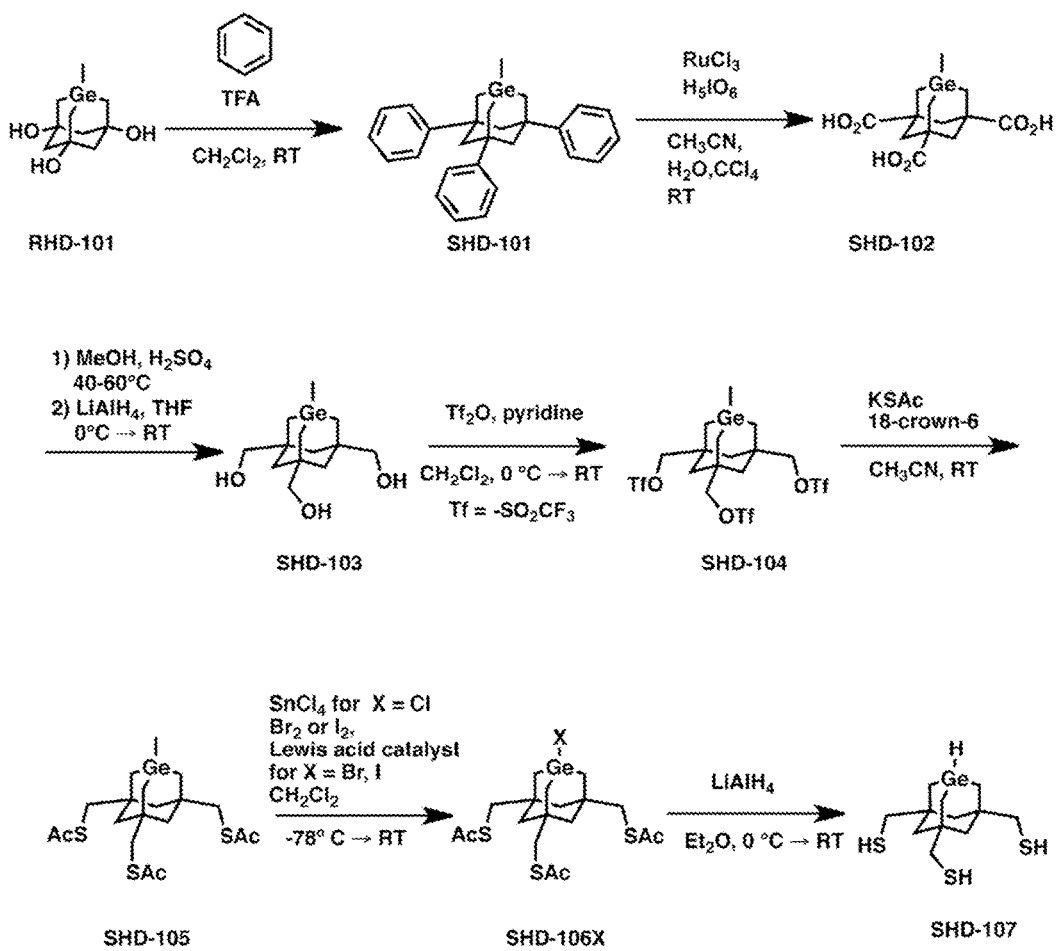
FIG. 35 depicts a synthetic route for the HDonationS tip.

FIG. 35 depicts a synthetic pathway for HDonationS. The synthesis steps are as follows: Allowing RHD-101 to react with benzene and trifluoroacetic acid (TFA) at room temperature in dichloromethane forms the triphenylgermaadamantane SHD-101. Oxidative cleavage of the phenyl groups with catalytic RuCl3 in a solvent mixture of CCl4, CH3CN, and H2O with periodic acid added as stoichiometric oxidant cleaves the aromatic rings between 0° C. to room temperature gives the tricarboxylic acid SHD-102. Esterification of SHD-102 with methanol with sulfuric acid between 40-60° C. gives the triester that can subsequently be reduced with LiAlH4 at 0° C. to give the triol SHD-103. Triol SHD-103 can be treated with triflic anhydride at 0° C. with pyridine in dichloromethane to give the triflate SHD-104. Displacement of the triflate groups with potassium thioacetate in the presence of 18-crown-6 ether in acetonitrile at room temperature yields the acetate-protected thiols in SHD-105. Treatment of SHD-105 with a Lewis acid source including to but not limited to SnCl4, I2, or Br2 in dichloromethane at −78° C. to room temperature selectively cleaves the Ge-Me bond to give the respective Ge—X (X=Cl, Br, I) bond in SHD-106X. Treating the resulting Ge—X compound SHD-106X with LiAlH4 at 0° C. to room temperature reduces the Ge—X bond as well as simultaneously removing the thioacetate groups from the thiols to yield the trithiol SHD-107, the HDonationS tip, upon aqueous workup.

Figure 36:
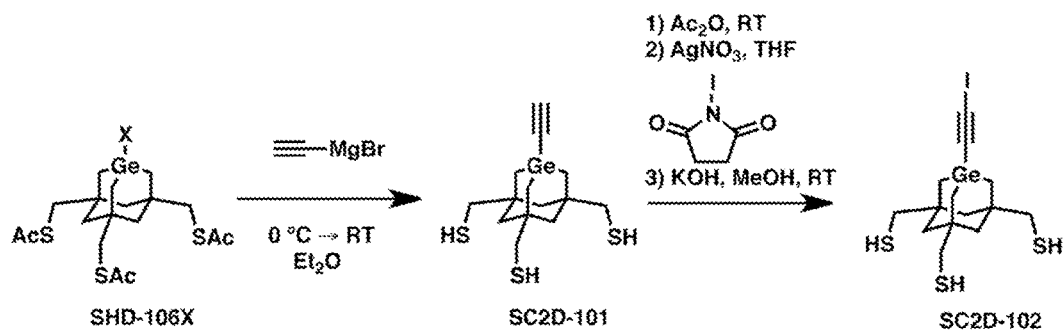
FIG. 36 depicts a synthetic route for the C2DonationS tip.

FIG. 36 depicts a synthetic pathway for C2DonationS. The synthesis steps are as follows: The intermediate SHD-106X from the HDonationS synthesis is allowed to react with an excess of commercially available ethynylmagnesium bromide solution in diethyl ether at 0° C. to room temperature to form SC2D-101. The excess of the ethynylmagnesium bromide ensures full deprotection of the thioacetate protective groups upon aqueous workup. The thiols in SC2D-101 are protected with acetate groups by treating it with acetic anhydride (Ac2O). The protected compound is then treated with silver nitrate and a slight excess of N-iodosuccinimide in THF at room temperature to form the iodoalkyne in SC2D-102. Subsequent treatment of the crude reaction mixture in basic methanol at room temperature yields SC2D-102, the C2DonationS tip.

Figure 37:
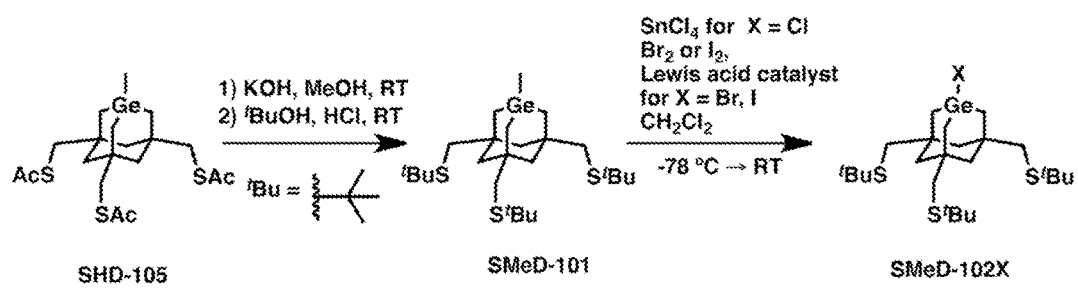
FIG. 37 depicts a synthetic route for the MeDonationS tip.
Figure 37:
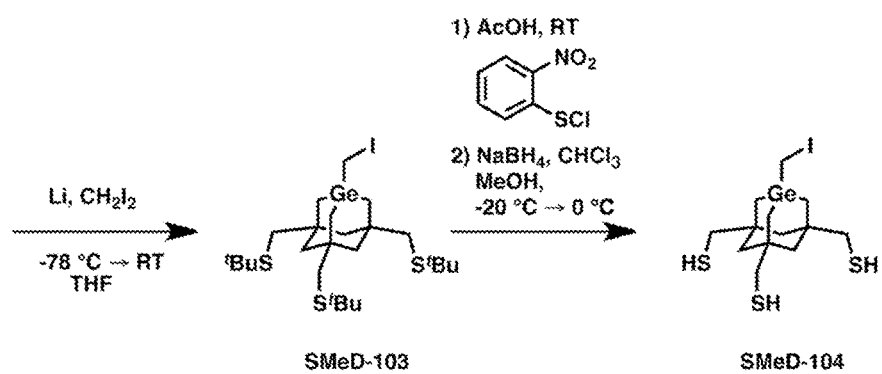

FIG. 37 depicts a synthetic pathway for MeDonationS. The synthesis steps are as follows: The synthesis of the thiol methyl donation tool begins from intermediate SHD-105. The acetate groups must be exchanged with a thioether protective group, specifically the tert-butyl group, to withstand the synthetic conditions. The acetate groups are removed in basic methanol at room temperature and then subsequently treated with an acidic solution of tert-butanol at room temperature to form SMeD-101. The Ge—Me bond is cleaved with a Lewis acid between −78° C. and room temperature with a reagent such as SnCl4, I2, or Br2 to yield the Ge—Cl bond in SMeD-102X. Treating SMeD-102X with lithium metal and excess CH2I2 at 0 C in THF at high dilution yields SMeD-103. Removal of the tert-butyl groups is performed with 2-nitrobenzenesulfenyl chloride in acetic acid and yields a mixed disulfide (Pastuszak, J. J., Chimiak, A., J. Org. Chem., 1981, 46, 1868. Quintela, J. M., Peinador, C., Tetrahedron, 1996, 52, 10497). Treating this disulfide with NaBH4 at low temperature between −20° C. and 0° C. allows the recovery of the free thiol SMeDon-104, the MeDonationS tip, without reducing the C—I bond.

Figure 38:
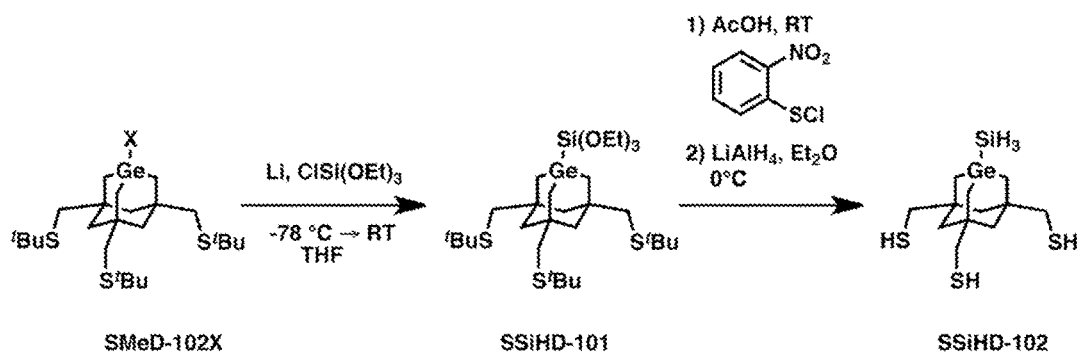
FIG. 38 depicts a synthetic route for the SiH3DonationS tip.

FIG. 38 depicts a synthetic pathway for SiH3DonationS. The synthesis steps are as follows: Intermediate SMeD-102X with t-butyl protected thiols is treated with lithium metal in THF at 0° C. followed by the addition of triethoxychlorosilane to give SSiHD-101 upon workup. This reaction forms the Ge—Si bond necessary for the SiH3 donor. The removal of the t-butyl groups is performed with the reagent 2-nitrobenzenesulfenyl chloride in acetic acid at room temperature to give the mixed disulfide. Treatment with LiAlH4 cleaves the S—S bonds to give the free thiols in SSiHD-102, the SiH3DonationS tip, as well as simultaneously reducing the triethoxysilyl group to —SiH3.

Figure 39:
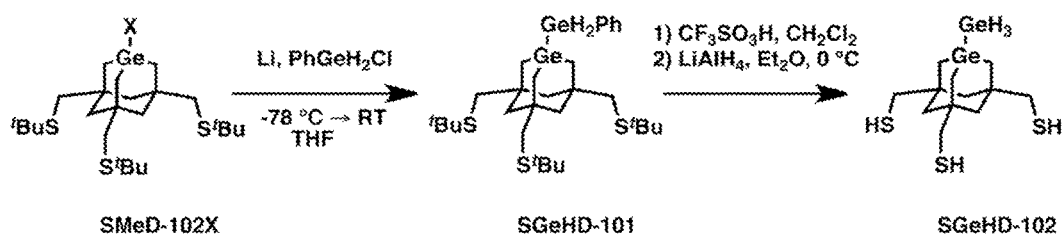
FIG. 39 depicts a synthetic route for the GeH3DonationS tip.

FIG. 39 depicts a synthetic pathway for GeH3DonationS. The synthesis steps are as follows: Intermediate SMeD-102X with t-butyl protected thiols is treated with lithium metal in THF at −78° C. The solution is then removed by syringe to separate the lithiated germanium species from the unreacted lithium metal and then slowly added dropwise to a solution of PhGeH2Cl at 0° C. to give SGeHD-101 upon workup. This reaction forms the Ge—Ge bond necessary for the —GeH3 donor. Treatment of SGeHD-101 with triflic acid cleaves the Ph-Ge bond to form a Ge—OSO2CF3 bond. Triflic acid also removes of the t-butyl thioether groups. Treatment of the this intermediate with LiAlH4 in diethyl ether at 0° C. cleaves any S—S bonds to give the free thiols in SGeHD-102, the GeH3DonationS tip, as well as simultaneously reducing the Ge triflate group to —GeH3.

Figure 40:
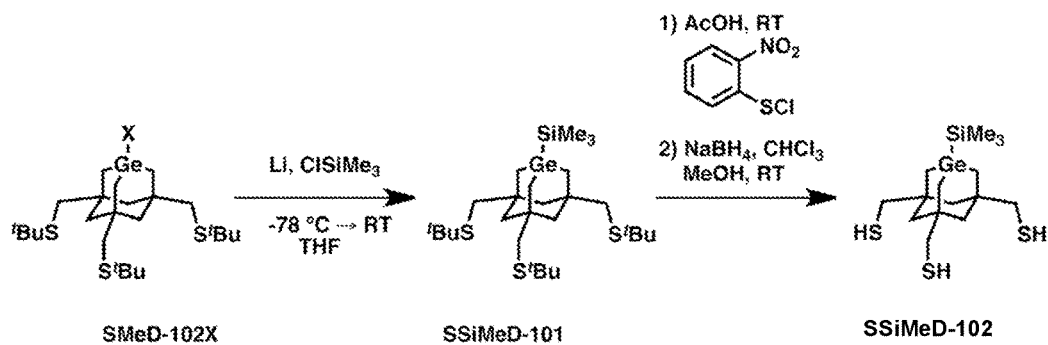
FIG. 40 depicts a synthetic route for the SiMe3DonationS tip.

FIG. 40 depicts a synthetic pathway for SiMe3DonationS. The synthesis steps are as follows: Intermediate SMeD-102X with t-butyl protected thiols is treated with lithium metal in THF at −78 C followed by the addition of chlorotrimethylsilane upon warming to 0° C. Upon workup the compound SSiMeD-101 with the Ge—Si bond is obtained. The removal of the t-butyl groups is performed with the reagent 2-nitrobenzenesulfenyl chloride in acetic acid at room temperature to give the mixed disulfide. Treatment with NaBH4 in chloroform and methanol at room temperature cleaves the S—S bonds to give the free thiols in SSiMeD-102, the SiMe3DonationS tip.

Figure 41:
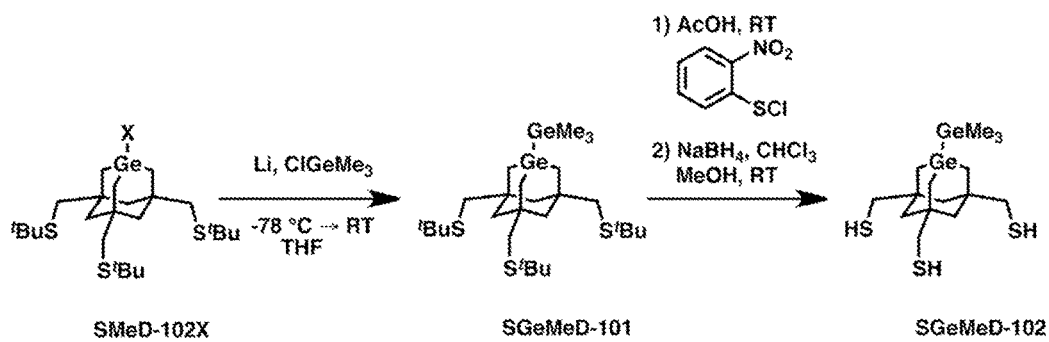
FIG. 41 depicts a synthetic route for the GeMe3DonationS tip.

FIG. 41 depicts a synthetic pathway for GeMe3DonationS. The synthesis steps are as follows: Intermediate SMeD-102X with t-butyl protected thiols is treated with lithium metal in THF at −78 C. The solution is then removed by syringe to separate the lithiated germanium species from the unreacted lithium metal and then slowly added dropwise to a solution of chlorotrimethylgermane at 0 C. Upon workup the compound SGeMeD-101 with the Ge—Ge bond is obtained. The removal of the t-butyl groups is performed with the reagent 2-nitrobenzenesulfenyl chloride in acetic acid at room temperature to give the mixed disulfide. Treatment with NaBH4 in chloroform and methanol at room temperature cleaves the S—S bonds to give the free thiols in SGeMeD-102, the GeMe3DonationS tip.

Figure 42:
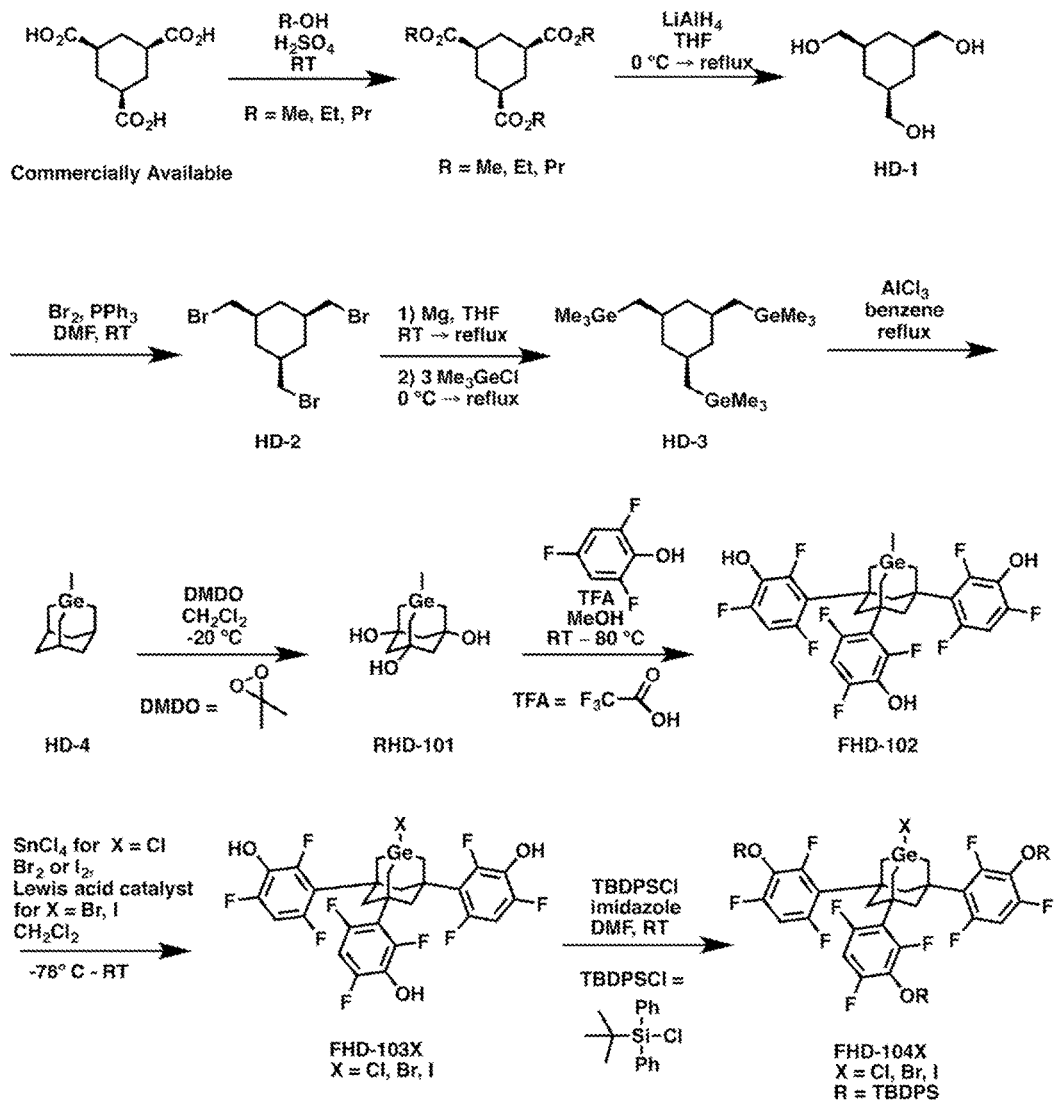
FIG. 42 depicts a synthetic route for the FHD-104X intermediate.

FIG. 42 depicts a synthetic pathway for intermediate FHD-104X, from which some of the other syntheses begin. The synthesis steps are as follows: Cis, cis-Tri-O-alkyl 1,3,5-Cyclohexanetricarboxylate is reduced with lithium aluminum hydride in refluxing THF and vigorous mechanical stirring to yield cis, cis-1,3,5-tris(hydroxymethyl)cyclohexane HD-1. The procedure used resembles that found in Boudjouk et al., Organometallics 1983, 2, 336. Cis, cis-1, 3,5-Tris(hydroxymethyl)cyclohexane, HD-1, is brominated utilizing triphenylphosphine dibromide generated in situ. This is accomplished by slow addition of bromine to a solution of the triol and triphenylphosphine in DMF at room temperature to yield cis, cis-1,3,5-tris(bromomethyl)cyclohexane, HD-2. The procedure used resembles that found in Boudjouk et al., Organometallics 1983, 2, 336. The tri-Grignard is generated in situ by adding cis, cis-1,3,5-Tris (bromomethyl)cyclohexane, HD-2, at room temperature to magnesium turnings in THF and heating to reflux. The tri-Grignard is then transferred to a second reaction vessel to separate the reagent from the excess magnesium turnings (Mg is capable of inserting into a Ge—Cl bond). Trimethylchlorogermane, previously dried over calcium hydride and degassed, is added slowly dropwise to the reaction at 0 C. After 2 hours, the reaction is warmed to room temperature for two hours, and finally refluxed overnight. The reaction yields predominantly cis, cis-1,3,5-Tris(trimethylgermylmethyl)cyclohexane, HD-3. Cis, cis-1,3-dimethyl-5-(trimethylgermylmethyl)cyclohexane and cis, cis-1-methyl-3,5-bis (trimethylgermylmethyl)cyclohexane are also produced in small amounts. The procedure used is similar to that found in Boudjouk and Kapfer, Journal of Organometallic Chemistry, 1983, 296, 339. HD-3 in benzene solution is subjected to redistribution reaction conditions using high purity anhydrous aluminum trichloride and heating to reflux to yield 1-methyl-1-germaadamantane. HD-3 side products cis, cis-1,3-dimethyl-5-(trimethylgermylmethyl)cyclohexane and cis, cis-1-methyl-3,5-bis(trimethylgermylmethyl)cyclohexane may also be present in the reaction or isolated and reacted under these conditions to yield HD-4 as well. HD-4 is reacted with excess "ketone free" dimethyldioxirane (DMDO) (Crandall, J. K. 2005. Dimethyldioxirane. e-EROS Encyclopedia of Reagents for Organic Synthesis.) in methylene chloride solution at −20 C to yield 1-methyl-3,5,7-trihydroxy-1-germaadamantane RHD-101. The absence of acetone in the reaction conditions allows for RHD-101 to precipitate from the reaction mixture, preventing over-oxidation. Upon completion of the reaction, isopropyl alcohol is used to quench the excess DMDO, preventing over-oxidation by excess reagent during reaction workup. RHD-101 is subjected to strongly acidic conditions in the presence of 2,4,6-trifluorophenol at room temperature to yield FHD-102. The use of Brønsted acidic conditions favors carbocation formation at the 3,5,7 bridgehead positions of the adamantane cage structure over redistribution reactivity at the germanium center. The 1-methyl group of FHD-102 can be exchanged with a halide (X=F, Cl, Br, I) with a variety of electrophilic reagents at low temperatures ranging from −78 C up to room temperature, depending on the halide desired. Reagents include, but are not limited to: Lewis acids such as SnCl4 or GaCl3, elemental halides Br2 and I2 with Lewis acid catalyst, alkyl halides such as isopropyl chloride with Lewis acid catalyst, and interhalogen compounds such as IBr and ICl. Furthermore, heavier FHD-103X halides can be converted to lighter halides utilizing the appropriate lighter silver halide (e.g. FHD-103Br and AgCl will produce FHD-103Cl). The phenolic alcohols of FHD-103X (X=F, Cl, Br, I) can be protected utilizing tert-butyl(chloro)diphenysilane and imidazole in DMF at RT to yield FHD-104X (X=F, Cl, Br, I).

Figure 43:
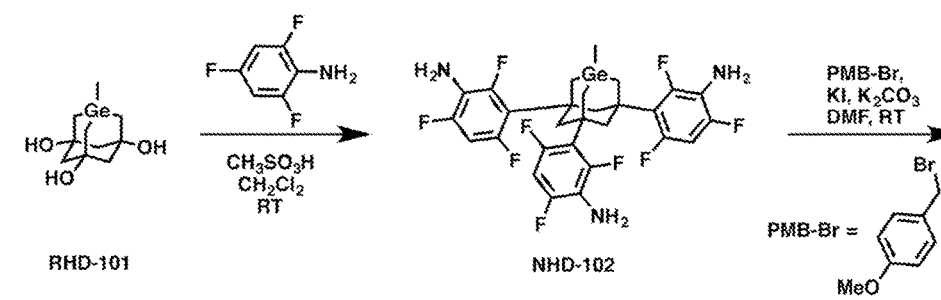
FIG. 43 depicts a synthetic route for the NHD-103X intermediate.
Figure 43:
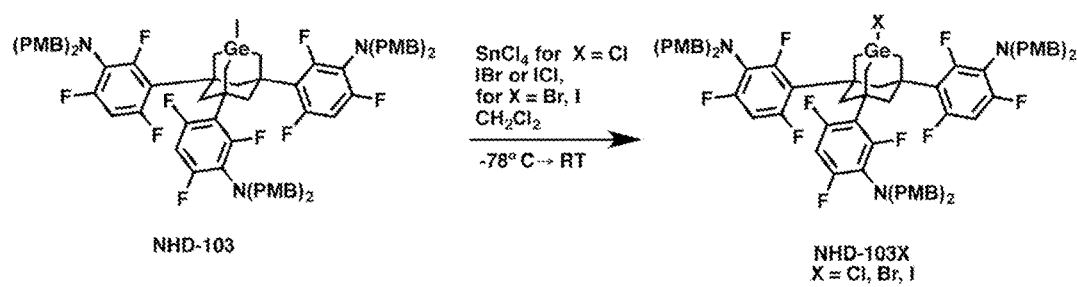

FIG. 43 depicts a synthetic pathway for intermediate NHD-103X, from which some of the other syntheses begin. The synthesis steps are as follows: RHD-101 is subjected to strongly acidic conditions such as methanesulfonic acid in the presence of 2,4,6-trifluoroaniline at room temperature to yield NHD-102. The use of Brønsted acidic conditions favors carbocation formation at the 3,5,7 bridgehead positions of the adamantane cage structure over redistribution reactivity at the germanium center. To form NHD-103, NHD-102 is alkylated at room temperature with 4-methoxybenzyl bromide in DMF with potassium carbonate base in the presence of potassium iodide. To form NHD-103X, the 1-methyl group of NHD-103 can be exchanged with a halide (X=F, Cl, Br, I) with a variety of electrophilic reagents at low temperatures ranging from −78 C up to room temperature depending on the halide desired. Reagents include, but are not limited to: Lewis acids such as SnCl4 or GaCl3, elemental halides Br2 and I2 with Lewis acid catalyst, alkyl halides such as isopropyl chloride with Lewis acid catalyst, and interhalogen compounds such as IBr and ICl. Furthermore, heavier NHD-103X halides can be converted to lighter halides utilizing the appropriate lighter silver halide (e.g. NHD-103Br and AgCl will produce NHD-103Cl).

Surface Preparation

Two exemplary surfaces are described herein, silicon and gold. More specifically, partially-hydrogenated partially-chlorinated Si(111), and atomically-flat Au(111).

Partially-hydrogenated partially-chlorinated Si(111) reduces the energy barrier to the tip molecules binding as compared to just chlorinated Si(111) because the hydrogen, being smaller in size than Cl, helps reduce steric congestion as the tip approaches the surface. Hydrogenation is preferably in the 33%-50% range, although wider ranges will work, as will not using hydrogenation at all. Partially hydrogenated partially-chlorinated Si(111) can be prepared in a number of ways. One is the following.

Clean, atomically flat doped Si(111) surfaces are prepared by direct current annealing the Si for several hours at ~650C followed by rapid heating to ~1200C for 1-20 sec while keeping the chamber pressure <1×10-9 Torr. This procedure gives the 7×7 reconstructed Si(111) surface, as in J Phys Cond Matt 26, 394001 (2014).

The Si(111) surface can be chlorinated by depositing Cl2 from an electrochemical cell similar to the one in J Vac Sci and Tech A 1, 1554 (1983), while the Si(111) is heated to ~400C. Atomically flat halogenated Si(111) surfaces have been prepared this way, as in Phys Rev Lett 78, 98 (1997).

Si(111)-Cl surfaces can then be partially hydrogenated by exposing the surface to 600 L of atomic hydrogen from a H2 cracker, as in Surf Sci 402-404, 170-173 (1998), with the Si(111)-Cl at room temperature.

Clean, atomically flat Au(111) surfaces are prepared by repeated cycles of sputtering and annealing a single crystal Au(111) surface, as in Phys Rev Lett 80, 1469 (1998).

Tip Bonding

Once synthesized, a tip can be bound to a presentation surface, a meta-tip surface, or a single-tip tool surface. Many ways of binding tips to surfaces are possible, and these may vary with the exact nature of the tip and the surface.

One method of depositing isolated tips on a surface is via thermal evaporation in vacuum. In this technique, purified molecules in the form of a solid or liquid are heated up in a vacuum chamber until they evaporate as a gas of isolated molecules. By placing the presentation surface within this gas, individual tips will adhere to the surfaced. (See tetramantane deposition in Nature Materials 7, 38 (2008)). This method has the advantage of depositing molecules without surface contamination from a solvent and can be used with masks to pattern a surface.

The tips having sulfur or thiol-based linkers will bond to gold spontaneously at room temperature. The tips with O or NH linkers designed to bond to chlorinated silicon surfaces require heating of the surface to overcome reaction barriers (hence the partial hydrogenation being favored as it keeps the activation barrier as far below the tip decomposition temperature as possible).

A simple way to evaporate molecules is to place the molecules in a glass or alumina crucible with a tungsten wire wrapped around the crucible. Passing a current through the wire heats the crucible and molecules, generating a molecular gas that exits the front of the crucible. A thermocouple on the crucible measures its temperature. A quartz crystal microbalance can be used to determine how much is evaporating as a function of time and temperature.

This is just one example of how tips could be bonded to a surface. Such techniques, including how to create sectors of specific molecules, are well-known in the respective arts. (Zahl, Bammerlin et al., "All-in-one static and dynamic nanostencil atomic force microscopy/scanning tunneling microscopy system," Review of Scientific Instruments, 2, 2005; Sidler, Cvetkovic et al., "Organic thin film transistors on flexible polyimide substrates fabricated by full-wafer stencil lithography," Sensors and Actuators A: Physical, 2, 2010; Vazquez-Mena, Gross et al., "Resistless nanofabrication by stencil lithography: A review," Microelectronic Engineering, 2015; Yesilkoy, Flauraud et al., "3D nanostructures fabricated by advanced stencil lithography," Nanoscale, 9, 2016)

Tip Activation

Figure 44:
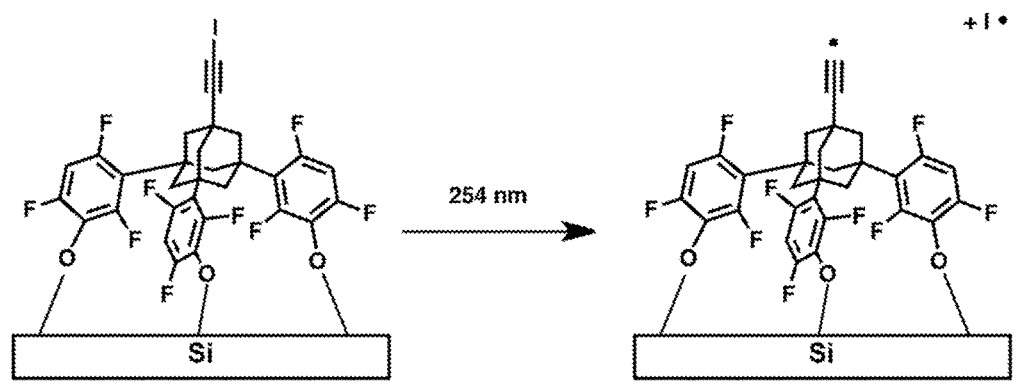
FIG. 44 depicts photo-activation of a halogen-capped tip.
Figure 45:
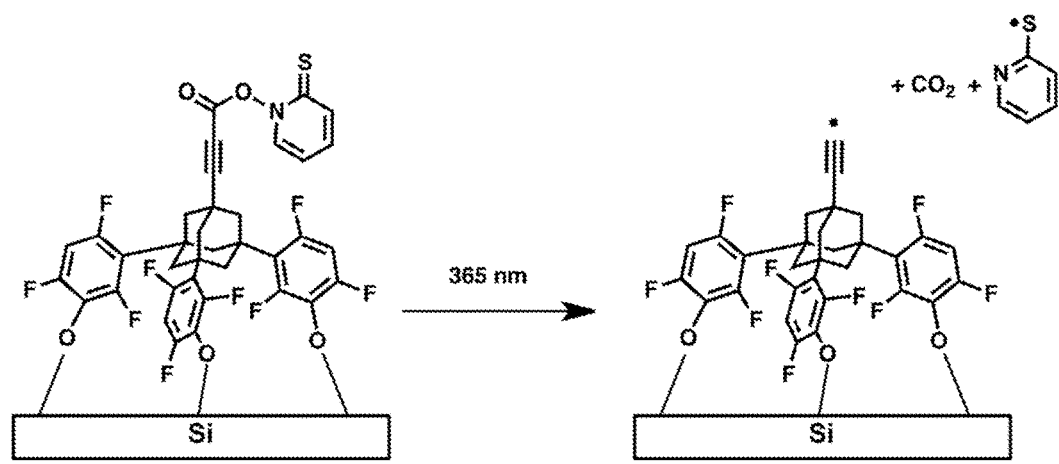
FIG. 45 depicts photo-activation of a Barton ester-capped tip.

Tips, particularly those with exposed radicals at their active site, may be bonded to a surface in an inactive form. One method of activating such tips is through photo-cleavage of the structure. For example, the halogen-capped tip examples herein can be activated through exposure to 254 nm light. FIG. 44 depicts an activating reaction for halogen-capped tips. Other wavelengths and chemistries can be used. For example, if different synthetic steps were used, a tip could be protected with a Barton ester, which can then be cleaved, activating the tip, with 365 nm light. FIG. 45 provides an example of the activation reaction that could be used with a Barton ester.

While not the only way to remove a tip cap, photo-activation is convenient in that different areas of a surface can be masked, or exposed to different wavelengths, making this a versatile technique even when multiple types of tips are desired on a single surface.

Barton Ester Caps

Other examples are provided herein of synthetic routes to halogen-capped tips, and how to activate them. To demonstrate another chemistry for synthesizing tips with protective caps, the Barton ester is an alternative that fragments upon being irradiated with, for example, 355-365 nm wavelength light to give the carbon centered radical, $CO_2$, and the pyrithiyl radical. (Barton, D. H. R., Crich, D., Potier, P. Tetrahedron Lett., 1985, 26, 5943-5946. For a review of thiohydroxamic acids chemistry see: Crich, D., Quintero, L. Chem. Rev. 1989, 89, 1413-1432) These types of activated molecules can be made from the described compounds and one such synthetic route is described below, resulting in the Barton ester version of the AbstractionO tip.

Figure 46:
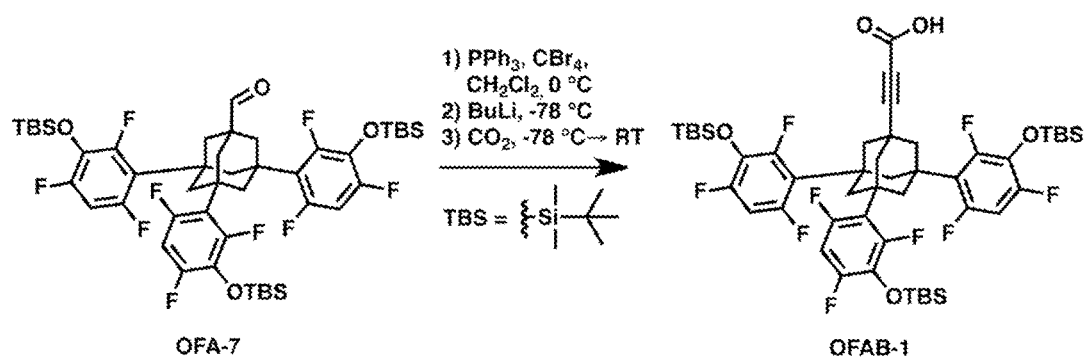
FIG. 46 depicts an exemplary synthesis of a tip with Barton ester cap.
Figure 46:
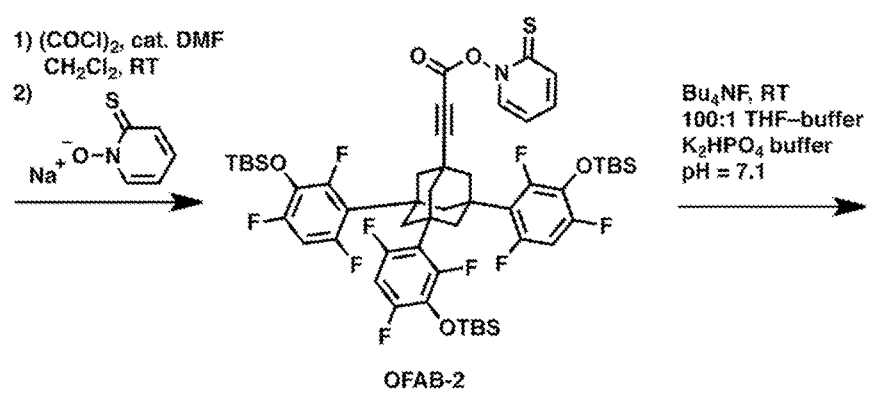
Figure 46:
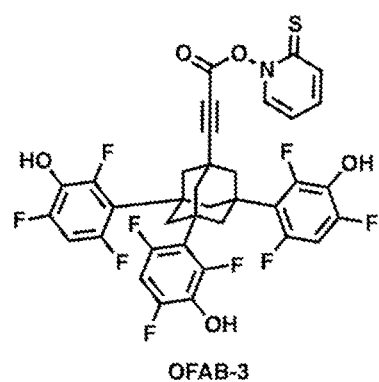

FIG. 46 depicts the synthesis of the Barton ester AbstractionO tip, which is as follows: To synthesize the Barton ester for photoactivation, propynoic acid OFAB-1 is made from OFA-7 using the traditional Corey-Fuchs procedure and quenching by bubbling gaseous $CO_2$ through the reaction mixture. (Corey, E. J., Fuchs, P. L. Tetrahedron Lett. 1972, 36, 3769-3772) The first step forms the 1,1-dibromoalkene in solution at −78 C. The addition of 2 more equivalents of butyllithium forms the lithium acetylide in the reaction mixture. By bubbling with the carbon dioxide the desired carboxylic acid OFAB-1 is obtained after an aqueous workup. To make the Barton ester, carboxylic acid derivative OFAB-1 is activated to the acid halide by oxalic acid and catalytic N,N-dimethylformamide (DMF) in dichloromethane at room temperature. To this reaction mixture the sodium pyrithione salt is added to the mixture to form the desired ester bond in compound OFAB-2. The Barton ester is unstable to aqueous acidic and basic media, so careful control of reaction conditions must be taken when removing the protective groups. Multiple techniques are possible for removal of silyl ethers such as OFAB-2 that are pH sensitive. One is to use more labile silyl ethers such as trimethylsilyl- (TMS-) or triethylsilyl- (TES-) ethers in place of the more stable TBS silyl ethers. Another method is to use OFAB-2 and catalytic solid tetra-n-butylammonium fluoride (TBAF) or cesium fluoride in 100:1 THF-buffer solution to produce OFAB-3. A solution of K2HPO4 buffered at pH=7.1 could be used in the TBAF deprotection. (DiLauro, A. M.; Seo, W.; Phillips, S. T., J. Org. Chem. 2011, 76, 7352-7358) This decreases the risk of hydrolyzing the Barton ester bond and increases the likelihood of obtaining the free phenols in OFAB-3, the Barton ester AbstractionO tip.

Using Tips

Figure 47:
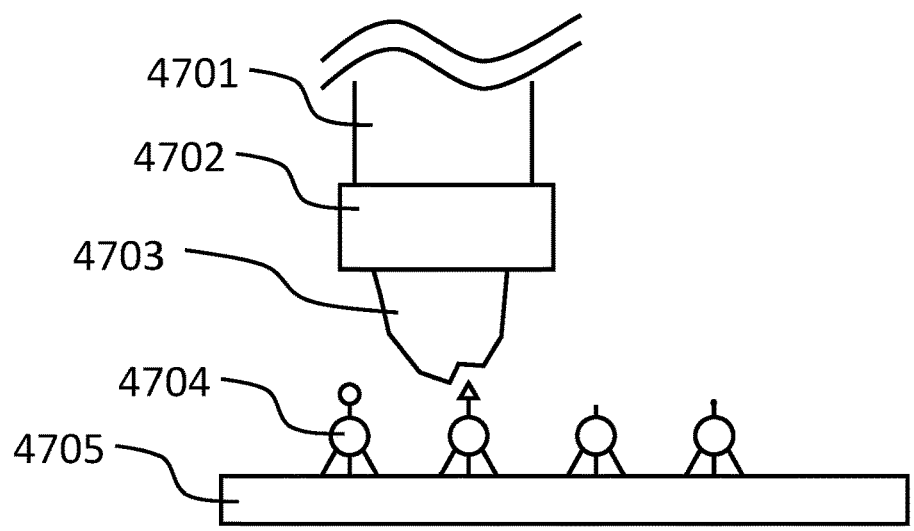
FIG. 47 depicts the use of surface-mounted tips where the workpiece moves.

One of the ways in which surface mounted tips can be used is depicted in FIG. 47. This figure is diagrammatic and not to scale. In FIG. 47, handle 4701 is connected to surface 4702. Surface 4702 is optional, serving to provide the desired materials and chemistry to bind workpiece 4703 in the case where the material of the handle is unsuitable for doing this directly. It is possible to bind workpiece 4703 directly to handle 4701. Handle 4701 would be connected to a positional means (not shown) for the purposes of moving handle 4701, and thereby workpiece 4703 with respect to tips (of which tip 4704 is representative) mounted on surface 4705.

In the depicted position, workpiece 4703 could be descending upon a tip, or it could be rising from just having used a tip. Regardless, the point is that surface 4705 can contain many tips, of many different types, including non-functional tips (which either failed to synthesize correctly or have already been used). Knowledge of tip position, for example, because sectoring was used to place certain tip types in certain locations, or via scanning the surface (before or during a build sequence), allows the workpiece to be moved to a desired tip, at which time a mechanosynthetic reaction occurs, and the workpiece then moves to the next desired tip. This process is repeated until the workpiece is complete.

Figure 48:
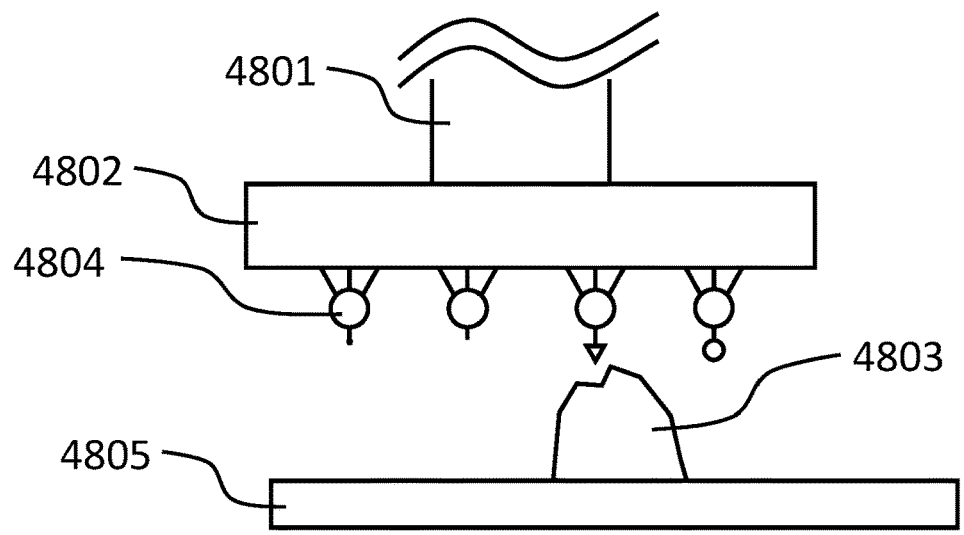
FIG. 48 depicts the use of surface-mounted tips where the surface moves.

Another way to use surface-mounted tips is to create a meta-tip, which is a handle upon which a plurality of tips may be mounted, directly, or via a surface. FIG. 48 depicts this mode of using surface-mounted tips, where handle 4801 is connected to (optional) surface 4802. Handle 4801 is also connected to a positional means (not shown). Tips, of which tip 4804 is representative, are shown mounted on surface 4802, but could be mounted directly to handle 4801. In this scenario, the tips move to act upon workpiece 4803, which resides upon surface 4805.

The main difference between the scenarios of FIG. 47 and FIG. 48 is whether the workpiece moves or the tips move. In actuality, it is possible that both move (e.g., one for course adjustments, one for fine), and the distinction is mainly one of equipment design.

FIG. 48 perhaps provides the clearest illustration of the advantages surface-mounted tips have over previous mechanosynthesis techniques. If surface 4802 only had one tip affixed to it, it would be analogous to the tips commonly used for mechanosynthesis. In this scenarios, it is obvious that to create complex workpieces, the affixed tip would have to a) be capable of multiple reactions and b) be regenerated frequently, or, the affixed tip would have to be frequently swapped to connect other tips to the positional means (not shown). Using either the scenario of FIG. 47 or FIG. 48 (and modifications thereof which would be obvious given the teachings herein), many tips are available to provide mechanosynthetic reactions, potentially (depending on the number of tips initially available and the number of reactions required to build the workpiece) without tip recharge and without tip swapping. Any reduction in tip recharge or tip swapping can help decrease the average time it takes to perform a reaction.

Note that surface-mounted tips could be used to build other atomically-precise tips, including building them directly onto the end of a handle or probe. This is another manner in which surface-mounted tips could be used to avoid a bootstrap sequence that uses non-atomically-precise tips.

Mechanosynthesis-Adapted Equipment

Efficient mechanosynthesis has a different set of requirements than typical SPM work. Typical SPM work involves analysis rather than manufacture, the point generally being to scan specimens to create an image or collect other data. Scan speed is frequently the limiting factor, and increasing scan speed is an active area of research (Dai, Zhu et al., "High-speed metrological large range AFM," Measurement Science and Technology, 9, 2015).

Scan speed is less important to systems for mechanosynthesis as long as the system can obtain the necessary accuracy without scanning. Ideally, other than perhaps scanning the surface initially to locate and identify tips, and perhaps scans of very small areas to check that a reaction occurred correctly, systems adapted for mechanosynthesis would not need to scan. Doing away with scanning for position refinement, and instead using metrology that allows the requisite point-to-point accuracy (meaning, moving directly from one tip or workpiece location to another, without using scanning in between to refine position), would considerably speed up the process of mechanosynthesis.

Note that while the ideal attributes for analytical or metrological SPM are different than those for systems for mechanosynthesis, even previous work on mechanosynthesis did not provide systems well-adapted for such work, due to the simple and low-volume nature of the work being performed.

Other useful adaptations that are somewhat unique to the requirements of mechanosynthesis include reducing tip recharge and reducing tip swapping (which does occur in more conventional uses of SPM equipment, but frequently because a tip has been damaged, not because many tips of different chemical natures are required, making the required frequency of tip swapping quite different). Surface mounted tips have been discussed herein as one way to reduce the need for tip recharge and tip swapping.

With respect to obtaining the necessary point-to-point accuracy (ideally sub-Angstrom, although less accuracy could be coupled with scanning of very small areas to precisely localize the tip), positional means capable of very high accuracy of large distances are available. For example, using Fabry-Perot interferometry, picometer-level accuracy has been shown to be possible at distances of 50 mm. (Lawall, "Fabry-Perot metrology for displacements up to 50 mm," J. Opt. Soc. Am. A, 12, OSA, 2005)

However, since mechanosynthetic reactions are generally not occurring exactly at the point being measured (which is generally, e.g., a reflective flat when using laser interferometry), such metrology still has to be carefully implemented to avoid, e.g., Abbe error which can be induced by slightly non-linear movement of the tip or workpiece with respect to, e.g., the reflective flat. One way to address this issue it to measure not only the X, Y and Z coordinates of the reflective flat, but also to measure (and so be able to account for) any rotation that might be occurring around these axis as well.

Figure 49:
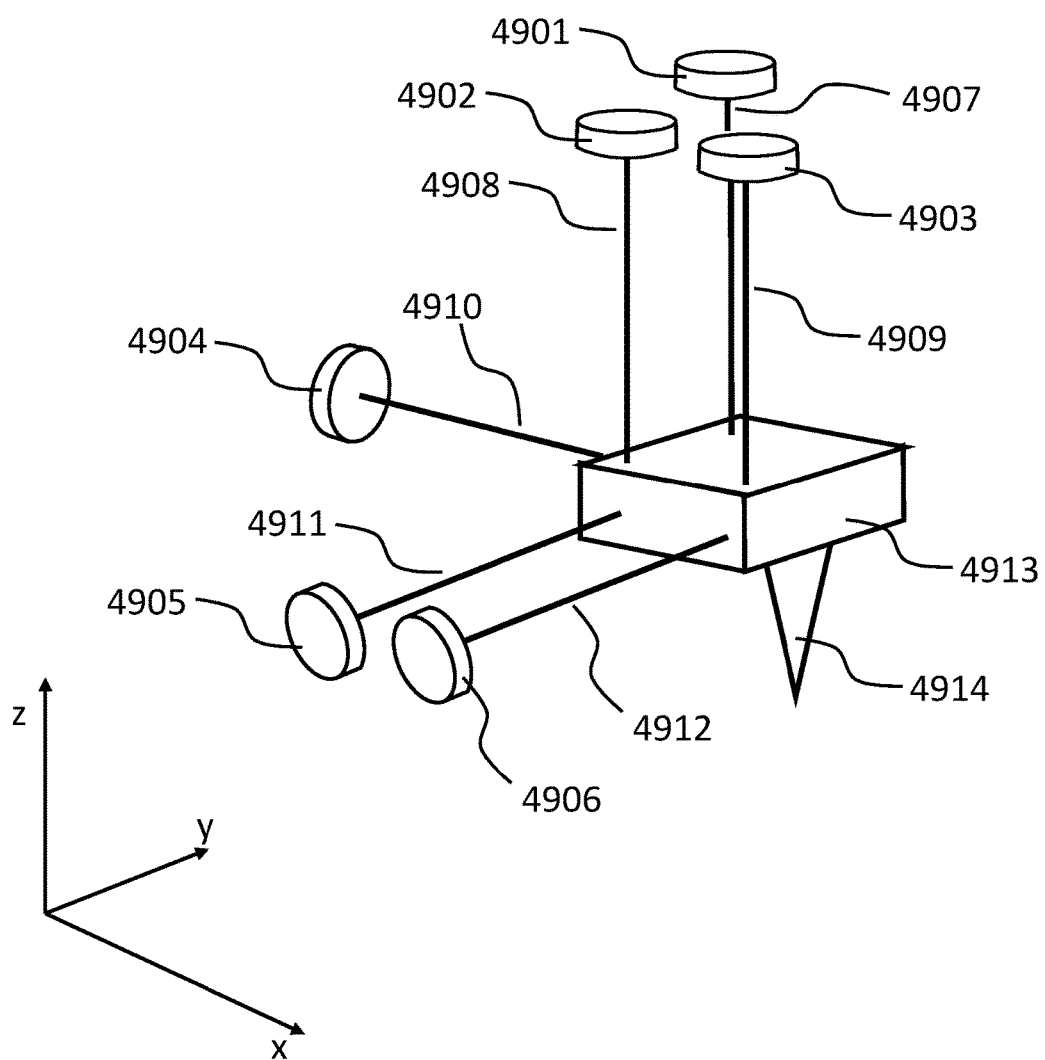
FIG. 49 depicts a metrology setup for measuring six degrees of freedom.

One way to measure both linear and angular position is to use 6 interferometers (e.g., Michelson or Fabry-Perot optical interferometers). FIG. 49 illustrates one way interferometers can be used to measure six degrees of freedom (X, Y, and Z, and rotation about each of those axes).

In FIG. 49, Reflective mirrors 4901-4906 and, and their respective beams, BeamZ1 4907, BeamZ2 4908, BeamZ3 4909, BeamX1 4910, BeamY1 4911 and Beam Y2 4912 can be used together to determine position in all six degrees or freedom. The spacing between various pairs of beams must be known to compute rotations. In this scenario, BeamX1 provides the X position. BeamY1 or BeamY2 provide the Y position. BeamZ1, or BeamZ2, or BeamZ3 provides the Z position. BeamZ1 and BeamZ2, together with the distance between the two beams allows the rotation about the X axis to be calculated. BeamZ2 and BeamZ3, together with the distance between the two beams allows the rotation about the Y axis to be calculated. And, BeamY1 and BeamY2, together with the distance between the two beams allows the rotation about the Z axis to be calculated.

Coupling the ability to provide, ideally, sub-Angstrom linear distance measurement over millimeter distances, while also measuring and accounting for angular errors, with, for example, a microscope that operates at 4K (room temperature is feasible but more technically challenging) in ultra-high vacuum, using a qPlus sensor, provides for a system that can access precise locations on large presentation surfaces with a greatly-reduced need to use scanning and image recognition to refine the relative position of a tip and the workpiece. These adaptations themselves are valuable for mechanosynthesis. Using such equipment with surface-mounted tips and the processes described herein provides systems adapted for mechanosynthesis that can provide much greater reaction throughput than conventional systems.

What is claimed is:

1. A tip, comprising:
    an adamantane body substituted with Ge at a bridgehead position;
    wherein said Ge constitutes an active site having feedstock bound thereto, said feedstock being selected from the group of,
    $CH_2$ radical, $SiH_3$, $GeH_3$, $SiMe_3$, and $GeMe_3$,
    and
    one or more legs, connected to said adamantane body at one or more positions which allow other tips or workpieces access to said active site for the purposes of carrying out a mechanosynthetic reaction.

2. The tip of claim 1 wherein said feedstock bound to said active site is $CH_2$ radical.

3. The tip of claim 1 further comprising SiH3 wherein said feedstock bound to said active site comprises $SiH_3$.

4. The tip of claim 1 wherein said feedstock bound to said active site comprises $GeH_3$.

5. The tip of claim 1 wherein said feedstock bound to said active site comprises $SiMe_3$.

6. The tip of claim 1 wherein said feedstock bound to said active site comprises $GeMe_3$.

* * * * *